(12) United States Patent
Pellicer et al.

(10) Patent No.: US 7,887,808 B2
(45) Date of Patent: Feb. 15, 2011

(54) HUMAN RGR ONCOGENE AND TRUNCATED TRANSCRIPTS THEREOF DETECTED IN T CELL MALIGNANCIES, ANTIBODIES TO THE ENCODED POLYPEPTIDES AND METHODS OF USE

(75) Inventors: Angel Pellicer, New York, NY (US); Peter Leonardi, East Haven, CT (US); Giorgio Inghirami, Mt. Vernon, NY (US)

(73) Assignee: New York University, New York, NY (US)

( * ) Notice: Subject to any disclaimer, the term of this patent is extended or adjusted under 35 U.S.C. 154(b) by 4 days.

(21) Appl. No.: 12/109,809

(22) Filed: Apr. 25, 2008

(65) Prior Publication Data

US 2008/0219993 A1 Sep. 11, 2008

Related U.S. Application Data

(62) Division of application No. 10/625,471, filed on Jul. 23, 2003, now Pat. No. 7,374,935.

(60) Provisional application No. 60/397,873, filed on Jul. 24, 2002.

(51) Int. Cl.
*A61K 39/395* (2006.01)
*C12P 21/08* (2006.01)
*G01N 33/567* (2006.01)
*G01N 33/48* (2006.01)

(52) U.S. Cl. ............ 424/155.1; 424/130.1; 424/135.1; 424/138.1; 424/141.1; 424/156.1; 424/172.1; 424/174.1; 435/7.1; 435/7.21; 435/7.23; 530/387.1; 530/387.3; 530/387.7; 530/387.9; 530/388.1; 530/388.85; 436/63; 436/64

(58) Field of Classification Search ............ 424/130.1, 424/135.1, 138.1, 141.1, 155.1, 156.1, 172.1, 424/174.1; 435/7.1, 7.21, 7.23; 436/63, 436/64; 530/387.1, 387.3, 387.7, 387.9, 530/388.1, 388.8, 388.85
See application file for complete search history.

(56) References Cited

FOREIGN PATENT DOCUMENTS

| WO | WO01/53312 | 7/2001 |
|---|---|---|
| WO | WO01/57278 | 8/2001 |

OTHER PUBLICATIONS

Corominas et al., Oncogene involvement in tumor regression: *H-ras* activation in the rabbit keratoacanthoma model, *Oncogene*, 6:645-651 (1991).
D'Adamo et al., *rsc:* A novel oncogene with structural and functional homology with the gene family of exchange factors for Ral, *Oncogene*, 14:1295-1305 (1997).
Hernandez-Muñoz et al., The Rgr oncogene (homologous to RalGDS) induces transformation and gene expression by activating Ras, Ral and Rho mediated pathways, *Oncogene*, 19:2745-2757 (2000).
Malumbres et al., Cellular response to oncogenic Ras involves induction of the Cdk4 and Cdk6 inhibitor p15$^{INK4b}$, *Molecular and Cellular Biology*, 20(8)2915-2925 (2000).
Accession No. AAA97456, CN1257923-A in database Geneseq, Gencore version 5.1.9 (Jun. 28, 2000).
Accession No. AAS34856, WO200155163-A1 in database Geneseq, Gencore version 5.1.9 (Aug. 2, 2001).
Adams, Accession No. AA311687, in *Nature*, 377(6547 Suppl):3-174 (1995).
Hedge, Accession No. AW962844 (Jun. 1, 2000).
Leonardi et al., *Oncogene*, 21:5108-5116 (Aug. 2002).
Miller et al., *Journal of Biological Chemistry*, 272(9):5600-5605 (1997).
Accession No. BI837800, (NIH-Mammalian Gene Collection) (Oct. 4, 2001).

*Primary Examiner*—Alana M Harris
*Assistant Examiner*—Anne L Holleran
(74) *Attorney, Agent, or Firm*—Browdy and Neimark, PLLC

(57) ABSTRACT

Naturally-occurring variants of human Rgr oncogene protein, in particular, abnormally truncated variants found in T cell malignancies, as well as the human Rgr protein are encompassed by the present invention. Also included are antibodies thereto and nucleic acid molecules encoding human Rgr protein and naturally-occurring variants thereof. The present invention further provides methods for diagnosing and treating T cell malignancies associated with abnormally truncated transcripts of human rgr oncogene and/or abnormal truncation of human Rgr protein.

6 Claims, 12 Drawing Sheets

FIG. 1

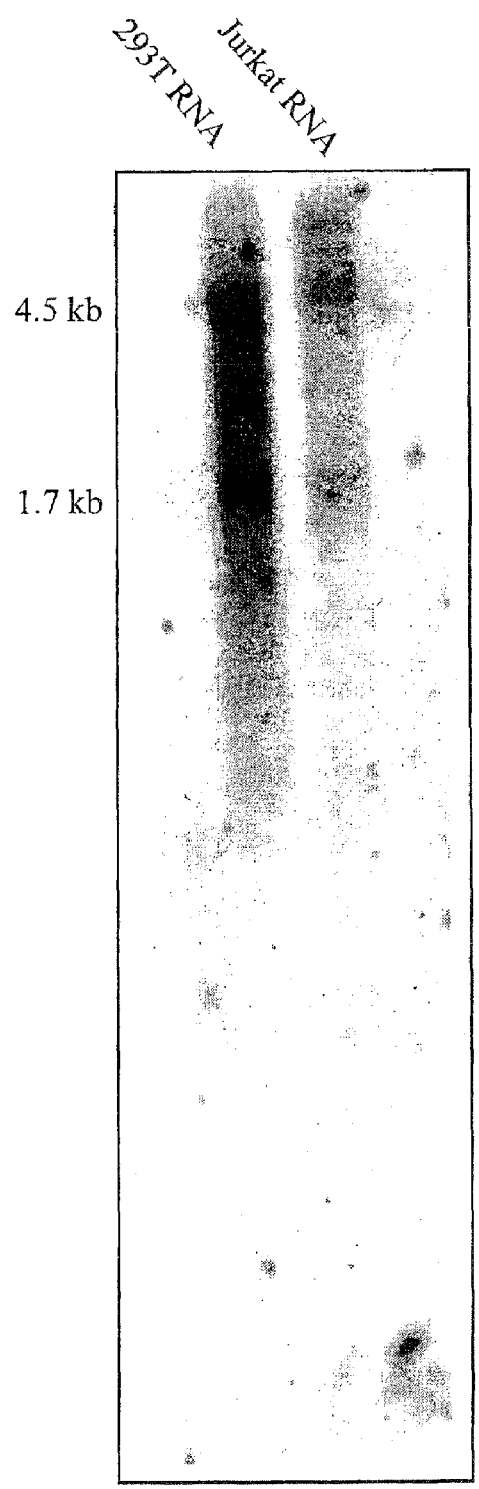
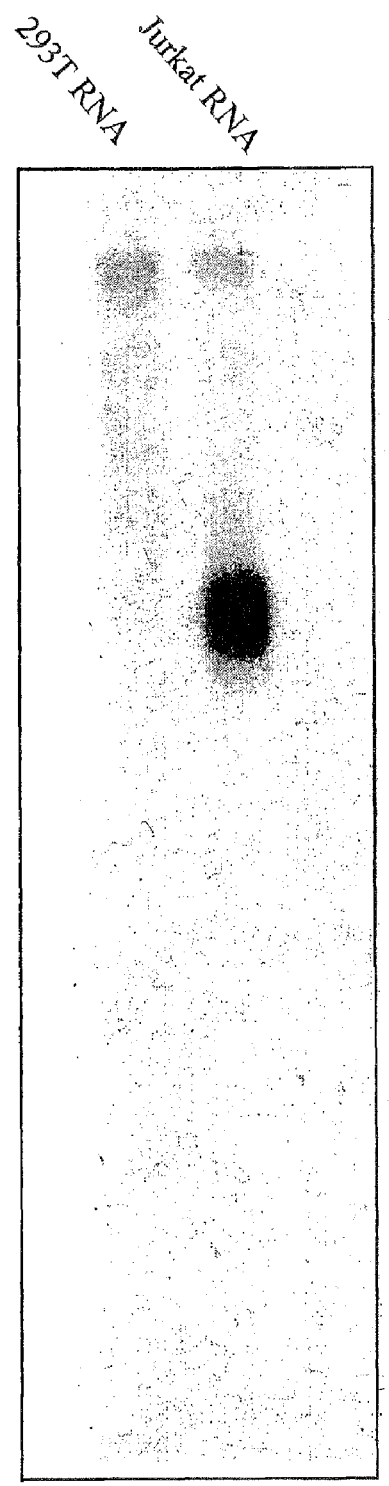
Probed with 5' hrgr
Probed with 3' hrgr
FIG.2B
FIG.2A

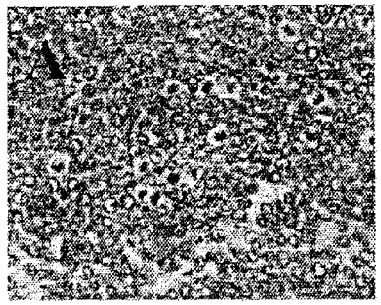
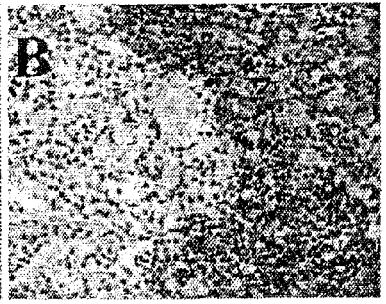
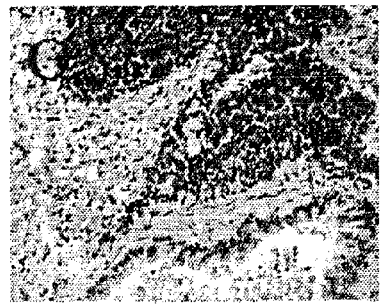
FIG. 8A    FIG. 8B    FIG. 8C
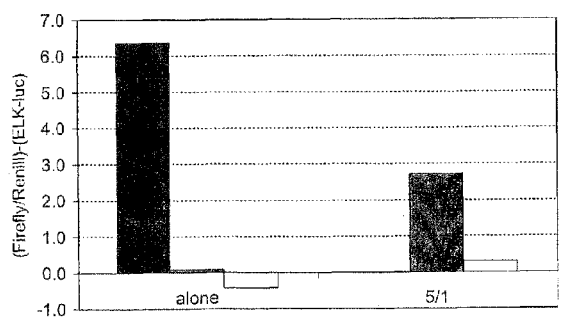
FIG. 9
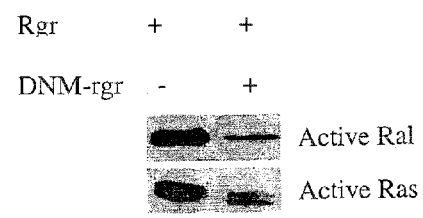
FIG. 10

CFP-Rgr

CFP-Rgr

DN1 → DN2 → DN3 → DN4 → DP → SP
| | Wil-type | CD4-RGR |
|---|---|---|
| DN<br>CD4-CD8- | 3.8<br>+/-0.19 | 1.7<br>+/-0.06 |
| DP<br>CD4+CD8+ | 80.9<br>+/-1.06 | 36.9<br>+/-1.20 |
| SP-CD8<br>CD4-CD8+ | 2.3<br>+/-0.04 | 2.6<br>+/-0.49 |
| SP-CD4<br>CD4+CD8- | 13.0<br>+/-1.29 | 8.6<br>+/-0.77 |
| | Wil-type | CD4-RGR |
|---|---|---|
| DN1<br>CD44+++/CD25- | 36.3<br>+/-2.03 | 21.2<br>+/-0.17 |
| DN2<br>CD4+++/CD25++ | 2.1<br>+/-0.35 | 1.4<br>+/-0.04 |
| DN3<br>CD44+/CD25++ | 13.8<br>+/-84 | 11.4<br>+/-1.41 |
| DN4<br>CD44-/CD25- | 47.7<br>+/-3.22 | 65.9<br>+/-1.54 |
FIG.14
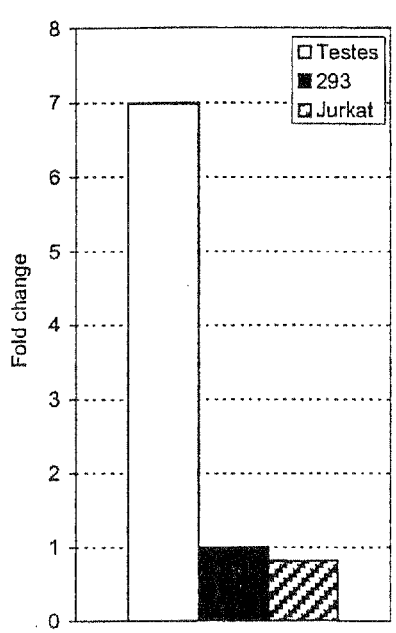
FIG.15A
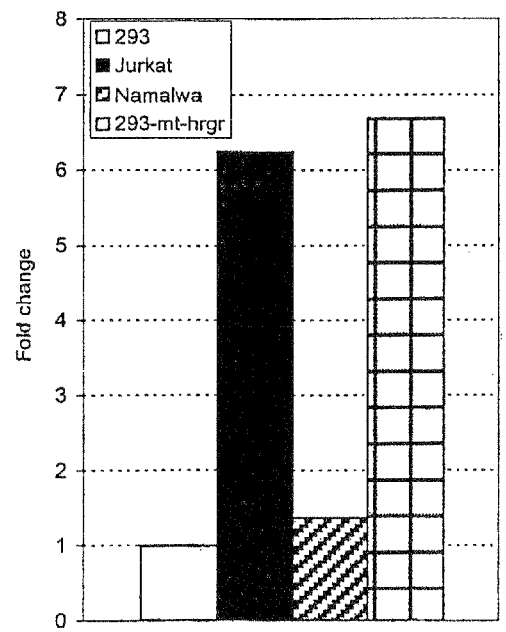
FIG.15B

US 7,887,808 B2

HUMAN RGR ONCOGENE AND TRUNCATED TRANSCRIPTS THEREOF DETECTED IN T CELL MALIGNANCIES, ANTIBODIES TO THE ENCODED POLYPEPTIDES AND METHODS OF USE

CROSS-REFERENCE TO RELATED APPLICATIONS

The present application is a divisional of application Ser. No. 10/625,471, filed Jul. 23, 2003, which claims priority from U.S. provisional application No. 60/397,873, filed Jul. 24, 2002. The entire contents of both applications are hereby incorporated by reference.

GOVERNMENT LICENSE RIGHTS

The experiments performed in this application were supported by the National Institutes of Health, Grant No. CA50434. The U.S. Government has a paid-up license in this invention and the right in limited circumstances to require the patent owner to license others on reasonable terms as provided by the terms of Grant No. CA 50434 awarded by the National Institutes of Health.

BACKGROUND OF THE INVENTION

1. Field of the Invention

The present invention relates to a human Rgr protein and naturally-occurring variants thereof, in particular, abnormally truncated variants found in T cell malignancies. The present invention also relates to antibodies that bind to the human Rgr protein and/or to naturally-occurring variants thereof and to nucleic acid molecules encoding human Rgr protein and naturally-occurring variants thereof.

2. Description of the Related Art

Analysis of the molecular bases of cancer have resulted in the identification of a number of genetic alterations affecting a subset of genes involved in control of proliferation, survival and differentiation. Oncogenes are one of the most prominent groups of genes involved in the pathogenesis of cancer and they often exert their transforming effects by subverting the normal signal transduction pathways in the host cell.

The laboratory of the present inventors first identified the rgr oncogene as one of the two components present in the rsc oncogene (D'Adamo et al., 1997), which was isolated from a DMBA-induced rabbit squamous cell carcinoma using gene transfer and the nude mouse tumorigenesis assay (Leon et al., 1988). Rgr is highly homologous to RalGDS, with a 40% overall identity, increasing to 72% over a 100 amino acid region. RalGDS is a guanine nucleotide exchange factor (GEF) that activates its effector, the Ral GTPase, by dissociating the bound GDP and allowing the binding of GTP which results in RalGDS activation (Albright et al., 1993; White et al., 1996). Like RalGDS, Rgr also dissociates GTP from Ral A (D'Adamo et al., 1997). The laboratory of the present inventors have further shown that rgr induces phosphorylation of ERKs, p38, and JNK kinases, and it increases the levels of GTP bound Ral and Ras (Hernandez-Muñoz et al., 2000). The importance of these activities is confirmed by experiments in which dominant negative Ras, Ral, and Rho block the transcription activation induced by rgr. However, only dominant negative Ras inhibits rgr transformation, indicating that Ras activation is crucial for the transforming activity of rgr (Hernandez-Muñoz et al., 2000).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides an isolated human Rgr protein comprising the amino acid sequence of SEQ ID NO:2, a fragment thereof, or a naturally-occurring variant thereof, which includes alternative splice variants and abnormally truncated variants of human Rgr.

The present invention also provides antibodies, or more generally molecules having the antigen binding portion of an antibody, that binds to the human Rgr protein or a naturally-occurring variant thereof and a pharmaceutical composition containing such antibodies/molecules. These antibodies/molecules are used in a method for diagnosing T cell malignancies associated with abnormal truncation of human Rgr protein and in a method for treating such T cell malignancies as further provided by the present invention.

Another aspect of the present invention is directed to isolated nucleic acid molecules, which encode the human Rgr protein, a fragment thereof, or a naturally-occurring variant thereof of the present invention, and a vector and a transformed host cell containing such a nucleic acid molecule.

Yet another aspect of the present invention provides a method for diagnosing T cell malignancies associated with abnormally truncated transcripts of human rgr oncogene and/or abnormal truncation of human Rgr protein by detecting amplification products using primers that would specifically only amplify abnormally truncated transcripts of human rgr.

Furthermore, an antisense oligonucleotide or a double stranded RNA complementary to the nucleic acid molecule of the present invention is provided along with a method of using the antisense oligonucleotide or double stranded RNA molecule to treat T cell malignancies associated with abnormally truncated transcripts of human rgr and/or abnormal truncation of human Rgr protein by inhibiting the production of abnormally truncated variant of human Rgr protein in T cells.

BRIEF DESCRIPTION OF THE DRAWINGS

FIG. 1 presents the nucleotide sequence of human rgr cDNA (SEQ ID NO:1) and the encoded amino acid sequence (SEQ ID NO:2). The initiating ATG is underlined and italicized. The intron exon junctions are denoted by vertical bars. The amino acid sequence deduced from the open reading frame is written in the one letter code below the corresponding codons. The nucleotide sequence that is conserved between the Jurkat transcript and the normal tissues is underlined. The first in frame stop codon has an asterisk underneath it. A possible alternative initiating ATG is underlined at position −440. A potential intron is highlighted, although it was not excised in any of the tissues that were tested. In some cases, an additional exon is present between the exons presented in this map (see FIG. 4).

FIGS. 2A and 2B are Northern blots showing that Jurkat cells express a short human rgr sequence. FIG. 2A shows a Northern blot analysis of 293T (human) and Jurkat (human) mRNA probed with the 3' region of the human rgr gene (exons 9-13). The large and small ribosomal bands are clearly visible at 4.5 kb and 1.7 kb. In FIG. 2B, an identical Northern filter probed with the 5' hypothesized region of the human rgr gene (exons 5-8).

FIG. 5D depicts 3T3 cells transfected with the empty vector. FIGS. 5E, 5F, and 5G show 10B, 10C, and 10E, respectively, which are 3T3 cell lines transfected with Jurkat clone 10 in the eukaryotic expression vector PCR 3.1. As shown in FIGS. 5E, 5F, and 5G, the cell lines are able to grow and form colonies in soft agar. FIG. 5H depicts a 3T3 cell line transfected with the PCR 3.1 empty vector.

FIGS. 8A-8C show hemataoxyline and eosin images of tumors in CD4-RGR transgenic mice. A representative section of a malignant thymic lymphoma in line 19, monomorphic population of large, non-cleaved lymphoid cells, with high mitotic index is shown in FIG. 8A. A section of a normal thymus from a wild type mouse of the same age is shown in FIG. 8B. In FIG. 5C, infiltration by lymphoma in the lung, patchy small infiltrates by monomorphic large-medium lymphocytes, is shown.

FIG. 9 is a graph showing rgr dominant negative mutant inhibition. A point mutant rgr can act as a dominant negative for the oncogene. This graph shows ratios of firefly to renilla luciferase activity after transient transfections of NIH-3T3 cells with rgr alone or in combination with a point mutant in the catalytic domain plus the reporter SRE-luc.

FIG. 10 is a Western blot showing the effect of dominant negative forms of rgr in Ras and Ral activation. 3T3 cells were transfected with only the oncogenic form of rgr or together with the Dominant Negative Mutant (DNM) of rgr, in a ratio 1:5 (rgr:DNM-rgr). Cell lysates were subjected to affinity precipitation with GST-RBD. Protein levels of Ras and Ral activated were determined by western blotting using a pool of K-Ras, N-Ras and H-Ras or Ral antibodies.

In FIG. 11A, COS-1 cells were transfected with CFP-Rgr. 24 hours after transfection, cells were serum starved overnight and imaged alive by LSM showing cytoplasmic distribution for Rgr. In FIG. 11B, COS-1 cells were co-transfected with CFP-Rgr and an excess of H-ras. 24 hours after transfection the cells were serum starved overnight and imaged alive by LSM. Rgr relocalized from cytosol to plasma membrane and Golgi. In FIG. 11C, COS-1 cells were co-transfected with YFP-RBD and the indicated CFP-tagged Ras isoform. 24 hours after transfection the cells were serum starved overnight and imaged alive by LSM. Ras activation, visualized by the redistribution of YFP-RBD, was only found for H-ras and N-ras in plasma membrane and Golgi. Arrows and asterisks indicate RBD recruitment to plasma membrane and Golgi, respectively.

In FIG. 13A, NIH-3T3 cells stably expressing Rgr were transfected using Oligofectamine reagent with the indicated increasing amounts of synthetic siRNA every 24 hours for 3 days. 48 hours after the last transfection, cells were harvested and assayed for BrdU incorporation. To suppress endogenous hRgr, Jurkat cells were transfected with either varying amounts of siRNA, a single strand RNA or nothing at all in FIG. 13B. In all the cases cells were grown in 10% serum. The transfection was repeated 3 times on consecutive days. On the $5^{th}$ day, cell cycle proliferation was determined by staining with propidium iodide. Values are relative to those obtained in untransfected Jurkat cells grown in 1% serum.

FIG. 14 shows that thymocyte development is altered in CD4-RGR mice. Primary thymocytes ($0.5 \times 10^6$ per point) were isolated from 7-week old wild type and CD4-RGR mice.

Figure 3:
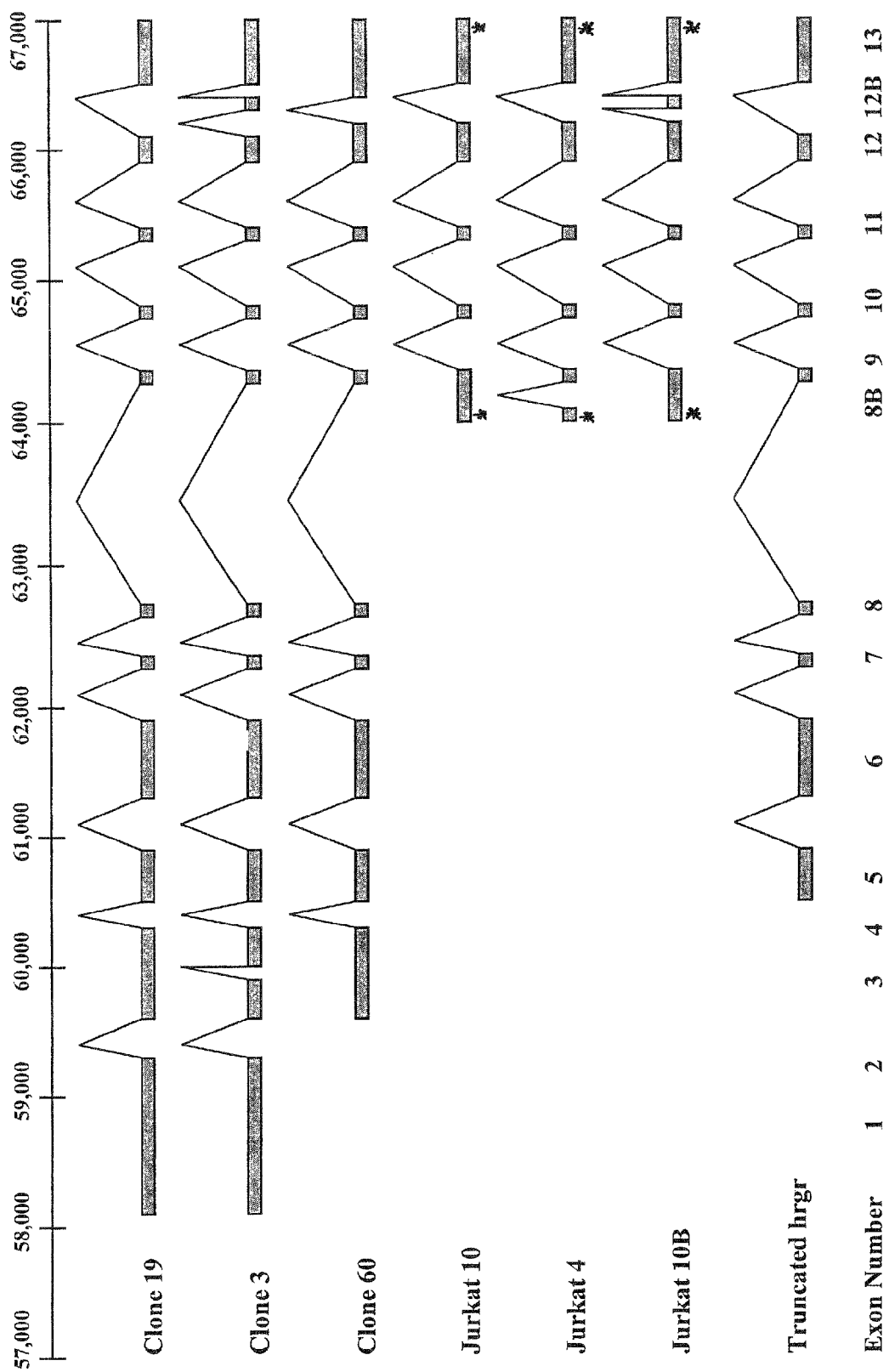
FIG. 3 schematically illustrates the exon map of the transcripts isolated from the Jurkat cell line and from human testes cDNA. Clones 19, 3, and 60 are from testes and Jurkat 4, 10, and 10B were isolated from Jurkat mRNA. The truncated hrgr shown here represents the human equivalent to the truncation found in rabbits (D'Adamo et al., 1997). The location of the exons on the BAC clone AP000347 corresponds to the line graph above the maps. The exon numbering lies below the maps. It should be noted that only the Jurkat truncated transcripts have the different varieties of exon 8B. The asterisks indicate the position of the primers that were chosen for 5' binding to detect the abnormally truncated hrgr transcripts. The 3' primer sequence is present in all hrgr transcripts isolated so far.

In order to determine the different stages of thymocyte development (see upper panel), CD4, CD8, CD44 and CD25 markers were simultaneously detected in both groups of thymocytes. Briefly, isolated thymocytes were washed twice with PBS and incubated at 4° C. for an hour with the following antibodies from CALTAG: PE-TexasRed-antiCD8, FITC-antiCD4, PE-antiCD44 and APC-antiCD25. Cells were then washed three times with PBS and fixed with 2% paraformaldehyde. Finally, cells were analyzed by flow cytometry. Left lower panel shows percentages of double negative (DN), double positive (DP), and single positive (SP) cells for CD4 and CD8 markers. Analysis of CD44 and CD25 markers among the DN thymocytes is shown in right lower panel. Gray highlighted boxes indicate values found for CD4-RGR samples that significantly differ from wild type values.

FIGS. 15A and 15B are graphs showing rgr abnormal transcripts are specifically expressed in Jurkat cells. Quantitative PCR was carried out with the iCycler iQ detection system from Biorad using a PCR Master mix (iQ SYBR Green Supermix, Biorad, CA) and specific primers for hrgr. Primers to 18S-rRNA were used as a control to normalize. The fold change in the evaluated samples is relative to the values in 293 cells. In FIG. 15A, RNA samples from human testes, 293 cells and Jurkat cells were used to amplify wild type hrgr. Specific primers are located in exon 4 (forward) and across the exon 4-5 boundary (reverse) for human full-length rgr (see FIG. 8A). As expected, wild type hrgr expression was only detected in human testes. To study the expression of the abnormal form of hrgr in Jurkat and Namalwa cells (a B-cell line), primers located in exon 8D (forward) and exon 9 (reverse) were used (FIG. 15B). 293 cells stably expressing a abnormal hrgr were used as a positive control.

DETAILED DESCRIPTION OF THE INVENTION

The laboratory of the present inventors has previously identified the oncogene rgr (ralGDS related) in DNA derived from a rabbit squamous cell carcinoma. In the example presented below, the identification of the human orthologue of the rabbit rgr gene termed hrgr (human ralGDS related) is described. Four alternatively spliced full-length hrgr transcripts were isolated from normal human testes and liver libraries. The present invention is further based on the discovery that truncation of hrgr confers transforming ability to its cDNA. Using a RT-PCR assay, the present inventors have been able to detect the expression of an abnormally truncated transcript in several human T cell lymphoma lines, and in fresh tissue samples of patients with T cell malignancies. In the DHL cell line, an Anaplastic Large Cell Lymphoma (ALCL) line, a DNA rearrangement was detected within the hrgr gene region. The present inventors propose that these T cell lymphomas, at least in part, owe their malignant phenotypes to genetic alterations of the hrgr gene. These findings also raise the possibility that mutations in the hrgr gene are involved in other malignancies.

The transcripts discovered by the present inventors encode alternatively spliced full-length human Rgr polypeptides or abnormally truncated human Rgr polypeptides. Accordingly, the present invention is intended to encompass both alternatively spliced and abnormally truncated human Rgr polypeptides and their encoding nucleic acid molecules.

The present invention provides an isolated polypeptide which is either (A) a human Rgr protein comprising the amino acid sequence of SEQ ID NO:2; (B) a fragment of (A) that has the activity of the human Rgr protein of SEQ ID NO:2, or (C) a naturally-occurring variant of (A). Naturally-occurring variants that are the result of alternative splicing or polymorphisms preferably have at least 90%, more preferably at least 95%, and most preferably at least 98% sequence identity to the full length human Rgr protein of SEQ ID NO:2. Non-limiting examples of alternatively spliced human Rgr polypeptides are presented in FIG. 3 as clones 19, 3 and 60 and in FIG. 4 as schemes 2, 3, and 4.

The naturally-occurring variant of the full length human Rgr protein of SEQ ID NO:2 can be an abnormally truncated variant which is intended to encompass those truncated variants in which part of the amino acid sequence is encoded by one or more exons that are not found in the nucleic acid molecule encoding the full length human Rgr protein. This part of the amino acid sequence comprises SEQ ID NO:6, which is encoded by exon 8D. Non-limiting examples of abnormally truncated variants of human Rgr encoded by the transcripts presented in FIG. 4 (transcripts 6, 7, 9, 10, 11, 12, and 14) or in FIG. 3 (Jurkat 4 and 10) have the amino acid sequence of SEQ ID NO:10 (transcript 6), SEQ ID NO:12 (transcript 7), SEQ ID NO:14 (transcript 9; Jurkat 10), SEQ ID NO:16 (transcript 10), SEQ ID NO:18 (transcript 11), SEQ ID NO:20 (transcript 12), SEQ ID NO:22 (transcript 14), or SEQ ID NO:24 (Jurkat 4).

The present invention also relates to an antibody, and more generally, to a molecule having the antigen binding portion of an antibody that binds to human Rgr protein or a naturally-occurring variant thereof. This molecule is intended to encompass a molecule which binds to an epitope in SEQ ID NO:6 (exon 8B) as well as a molecule which binds to an epitope present in both the human Rgr protein of SEQ ID NO:2 and an abnormally truncated variant thereof which comprises the amino acid sequence of SEQ ID NO:6.

It should be understood that when the term "antibodies" is used with respect to the antibody embodiments of the present invention, this is intended to include intact antibodies, such as polyclonal antibodies or monoclonal antibodies (mAbs), as well as proteolytic fragments thereof such as the Fab or F(ab')$_2$ fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, et al, 1990 and Gross et al, 1989). Single-chain antibodies can also be produced and used. Single-chain antibodies can be single-chain composite polypeptides having antigen binding capabilities and comprising a pair of amino acid sequences homologous or analogous to the variable regions of an immunoglobulin light and heavy chain (linked VH-VL or single-chain FV). Both VH and VL may copy natural monoclonal antibody sequences or one or both of the chains may comprise a CDR-FR construct of the type described in U.S. Pat. No. 5,091,513 (the entire content of which is hereby incorporated herein by reference). The separate polypeptides analogous to the variable regions of the light and heavy chains are held together by a polypeptide linker. Methods of production of such single-chain antibodies, particularly where the DNA encoding the polypeptide structures of the VH and VL chains are known, may be accomplished in accordance with the methods described, for example, in U.S. Pat. Nos. 4,946,778, 5,091, 513 and 5,096,815, the entire contents of each of which are hereby incorporated herein by reference.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

Polyclonal antibodies are heterogeneous populations of antibody molecules derived from the sera of animals immunized with an antigen.

Monoclonal antibodies (mAbs) are a substantially homogeneous population of antibodies to specific antigens. MAbs may be obtained by methods known to those skilled in the art. See, for example Kohler et al, (1975); U.S. Pat. No. 4,376, 110; Harlow et al, (1988); and Colligan et al, (1994-2001), the entire contents of which references are incorporated entirely herein by reference. Such antibodies may be of any immunoglobulin class including IgG, IgM, IgE, IgA, and any subclass thereof. The hybridoma producing the mAbs of this invention may be cultivated in vitro or in vivo. High titers of mAbs can be obtained by in vivo production where cells from the individual hybridomas are injected intraperitoneally into pristane-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity during application and to increase yields in production, for example, where murine mAbs have higher yields from hybridomas but higher immunogenicity in humans, such that human/murine chimeric or humanized mAbs are used. Chimeric and humanized antibodies and methods for their production are well-known in the art, such as Cabilly et al (1984), Morrison et al (1984), Boulianne et al (1984), European Patent 0 125 023 (1984), Neuberger et al (1985), European Patent 0 171 496 (1985), European Patent 0 173 494 (1986), WO 8601533 (1986), European Patent 0 184 187 (1986), Sahagan et al (1986); WO 9702671 (1987), Liu et al (1987), Sun et al (1987), Better et al (1988), and Harlow et al (1988). These references are hereby incorporated herein by reference.

A "molecule which includes the antigen-binding portion of an antibody," is intended to include not only intact immunoglobulin molecules of any isotype and generated by any animal cell line or microorganism, or generated in vitro, such as by phage display technology for constructing recombinant antibodies, but also the antigen-binding reactive fraction thereof, including, but not limited to, the Fab fragment, the Fab' fragment, the F(ab')$_2$ fragment, the variable portion of the heavy and/or light chains thereof, and chimeric or single-chain antibodies incorporating such reactive fraction, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

As discovered by the present inventors, abnormally truncated transcripts of human rgr oncogene and the abnormally truncated variants of human Rgr protein are present in T cell malignancies such as non-Hodgkin's lymphomas (NHL) derived from T cells. Non-limiting examples are presented in Table 1 of the example presented herein. Many of the tumors included in this class belong to many different subclasses that are based on some morphological features that may or may not correspond to their molecular pathogenic alterations. Given this heterogeneity, it has been difficult to establish accurate criteria for diagnostic classification and prognosis. In addition, there is a wide variation in the response of this group of tumors to therapy, with some of them having a short and fatal course.

A method of the present invention for diagnosing T cell malignancies associated with abnormal truncation of human Rgr protein involves contacting a sample containing T cells obtained from a human subject with a molecule having the antigen binding portion of an antibody according to the present invention and detecting the presence or absence of binding to any abnormally truncated variant of human Rgr protein in T cells of the sample. Detection of binding between the molecule of the present invention and an abnormally truncated variant of human Rgr protein provides a diagnosis of a T cell malignancy associated with abnormal truncation of human Rgr protein. This method preferably uses a molecule according to the present invention which binds an epitope in SEQ ID NO:8. Such a molecule would distinguish abnormally truncated variants containing the epitope from normal full-length human Rgr protein because the epitope recognized by this molecule is not present in normal full-length human Rgr protein.

Moreover, a molecule which binds to an epitope in both the normal Rgr protein of SEQ ID NO:2 and abnormally truncated variants as described above can also be used in this diagnostic method of the present invention. This is because normal full length human Rgr protein is expressed at a low level which is undetectable using antibody-based assay systems. However, as abnormally truncated variants are overexpressed due to the abnormal alteration/truncation at the DNA level, a molecule which binds to an epitope present in both the human Rgr protein of SEQ ID NO:2 and an abnormally truncated variant can also be used in the method of the present invention because positive detection using an antibody-based assay system means that there is overexpression (at least to a level detectable by antibodies), and overexpression would be caused by the abnormal alteration/truncation of the DNA encoding human Rgr. Ways of detecting binding between the molecule of the present invention and an abnormally truncated variant of human Rgr protein, i.e., ELISA, are well known and well practiced in the art.

The present invention further provides a composition, more specifically a pharmaceutical composition which includes the molecule having the antigen binding portion of an antibody according to the present invention and a pharmaceutically acceptable carrier, excipient, diluent, or auxiliary agent. This pharmaceutical composition can be used for passive immunization to treat T cell malignancies associated with abnormal truncation of human Rgr protein. Thus, a still further aspect of the present invention relates to a method for treating T cell malignancies associated with abnormal truncation of human Rgr protein which involves administering to a human subject in need thereof a molecule having the antigen binding portion of an antibody of the present invention, preferably in the form of a pharmaceutical composition, to bind and block the effect of an abnormally truncated variant of human Rgr protein in malignant T cells of the human subject.

Yet another aspect of the present invention provides an isolated nucleic acid molecule comprising a nucleotide sequence encoding the isolated polypeptide of the present invention, which nucleic acid molecule is preferably the human rgr full length transcript, alternatively spliced transcripts thereof, or abnormally truncated variants thereof. When the nucleic acid molecule is the DNA or human rgr transcript encoding the polypeptide comprising the amino acid sequence of SEQ ID NO:2, its nucleotide sequence preferably comprises nucleotides 1171 to 2589 of SEQ ID NO:1.

When the nucleic acid molecule is the DNA or human rgr transcript encoding an abnormally truncated variant of human Rgr protein, its nucleotide sequence preferably encodes an amino acid sequence comprising SEQ ID NO:8 (encoded by exon 8D) and more preferably comprises the nucleotide sequence of SEQ ID NO:5 (exon 8B), SEQ ID NO:6 (exon 8C), SEQ ID NO:7 (exon 8D), or a combination thereof joined together as a contiguous sequence (i.e., 8B+8C, 8B+8D, 8B+8C+8D, 8C+8D). Preferred embodiments of the nucleic acid molecule of the present invention include those comprising the nucleotide sequence of SEQ ID NO:9 (transcript 6 shown in FIG. 4), SEQ ID NO:11 (transcript 7), SEQ ID NO:13 (transcript 9; Jurkat 10), SEQ ID NO:15 (transcript 10), SEQ ID NO:17 (transcript 11), SEQ ID NO:19 (transcript 12), SEQ ID NO:21 (transcript 14), or SEQ ID NO:23 (Jurkat 4 shown in FIG. 3). Also provided are a vector comprising the nucleic acid molecule of the present invention and a host cell transformed with the nucleic acid molecule of the present invention.

A still further aspect of the present invention is directed to another method for diagnosing T cell malignancies associated with abnormally truncated transcripts of human rgr oncogene and/or abnormal truncation of human Rgr protein. This diagnosing method involves subjecting the nucleic acid molecule of the present invention, which is isolated from T cells obtained from a human subject, to amplification using a primer from the nucleotide sequence of the exon that is not present in normal full length human rgr and a primer from a nucleotide sequence which is present in both the nucleotide sequence encoding the abnormally truncated variant and nucleotides 1171 to 2589 of SEQ ID NO:1. A T cell malignancy associated with abnormally truncated transcripts of human rgr and/or abnormal truncation of human Rgr protein is diagnosed when the presence of amplification products corresponding to abnormally truncated transcripts of human rgr is detected by means well known in the art.

Additionally, the present invention provides an antisense oligonucleotide complementary to a messenger RNA, which is a nucleic acid molecule according to the present invention and which encodes an abnormally truncated variant of human Rgr protein, wherein this antisense oligonucleotide inhibits the production of an abnormally truncated variant of human Rgr protein. Antisense oligonucleotides can be screened by art-recognized methods of "gene walking" to obtain antisense that inhibits the production of the human Rgr protein or abnormally truncated variants thereof encoded by the nucleic acid molecule of the present invention.

The antisense oligonucleotide of the present invention can be used in a method for treating T cell malignancies associated with abnormally truncated transcripts of human rgr oncogene and/or abnormal truncation of human Rgr protein. This method involves causing the antisense oligonucleotide of the present invention to contact abnormally truncated DNA or transcripts of human rgr and inhibiting the production of an abnormally truncated variant of human Rgr protein in T cells of a human patient in need thereof.

A yet still further aspect of the present invention is a double stranded RNA molecule, one of whose strands is complementary to a messenger RNA which is a nucleic acid molecule according to the present invention and which encodes an abnormally truncated variant of human Rgr protein. This double stranded RNA molecule, which is a small interfering RNA (siRNA or sRNA; see McManus et al., 2002) or a precursor thereof, inhibits the production of an abnormally truncated variant of human Rgr protein. An example of a siRNA is the double stranded RNA molecule, taken from exon12 of the human rgr gene, with SEQ ID NO:27 as the sense strand and SEQ ID NO:28 as the antisense strand. Preferably, one strand of the double stranded RNA molecule is complementary to a nucleotide sequence that is present in abnormally truncated transcripts of human rgr oncogene but not present in normal full length human rgr.

Similarly, the double stranded RNA molecule of the present invention as described above can also be used in a method for treating T cell malignancies associated with abnormally truncated transcripts of human rgr oncogene and/or abnormal truncation of human Rgr protein where the double stranded RNA molecule is caused to contact abnormally truncated transcripts of human rgr and inhibit the production of human Rgr protein in T cells of a human patient in need thereof.

Having now generally described the invention, the same will be more readily understood through reference to the following examples which are provided by way of illustration and is not intended to be limiting of the present invention.

EXAMPLE

In this example, the present inventors have isolated the human orthologue of the rabbit rgr gene, hrgr. Moreover, the present inventors have also isolated mutant hrgr transcripts from lymphoid malignant cell lines and tissues. The observation that the hrgr gene is present in truncated forms in some types of T-cell lymphomas strongly suggests that hrgr has a pathogenic role in lymphoid neoplasms. The materials and methods used in the experiments disclosed in this example are presented below along with the results and a discussion.

Materials and Methods

Transfection

NIH 3T3 cells were transfected with the fusion constructs by the calcium phosphate method (Pellicer et al., 1980). The cells were then selected for the presence of the plasmid by growth in DMEM media with 10% bovine serum and G418, 200 µg/ml (Gibco).

Focus Formation Assay

NIH 3T3 cells were seeded at $2 \times 10^5$ per 10 cm plate. The following day, cells were transfected by the calcium phosphate method (Pellicer et al., 1980) using 2 ml of precipitate containing 100 ng or 1 µg of plasmid DNA with 10 µg of carrier DNA. After 12 hours of incubation at 37° C., the precipitate was removed and fresh DMEM+10% CS was added. Two days later, the cells were trypsinized and split 1:3 into 10 cm plates containing DMEM+5% CS. The cells were re-fed every 3-4 days and foci were scored under the microscope after 3 weeks.

Anchorage Independence Assay

Growth in soft agar of cell lines derived from NIH 3T3 cells was determined as described (Bouck and Di Mayorca, 1979). 5 ml of DMEM+10% CS and 0.63% agarose was poured into each 6 cm plate and allowed to solidify. Cells were trypsinized, counted and drawn through a 20 gauge needle to break up clumps. $5 \times 10^4$ cells in 0.9 ml were combined with 1.1 ml DMEM+10% CS and 0.38% agarose and poured onto the bottom agarose. It was particularly important to keep the agarose at 50° C. prior to use. The plates were allowed to harden in a sterile hood and then incubated at 37° C. for 2-3 weeks re-fed every week. Clusters of cells greater that 30 cells were scored as positives.

Growth in Low Serum $5 \times 10^4$ NIH 3T3 and the NIH 3T3-hrgr transfected cells were plated on 10 cm plates. Cells were grown in DMEM+1% CS. Cells were trypsinized and counted on a hemocytometer at days 1, 4, 8, and 11.

Screening of the Human Testes cDNA Library

The cDNA library purchased from Omnigene had been prescreened with PCR primers specific for the 3' Jurkat fragment of the hrgr cDNA. The method of PCR screening the cDNA library was as described by the manufacturer (Omnigene). Briefly, the cDNA library was subcloned into a PCR 3 eukaryotic expression vector. Bacteria provided by the company were pre-transformed with the cDNA library. An array of pools of bacteria was screened with PCR and the hrgr specific primers. Positive pools were divided into 96 smaller pools. This process was repeated 3 times and the still remaining positive pools were plated on ampicillin agar plates. Clones from the plates were picked and suspended in LB media. Aliquots of the clones were screened by PCR for the presence of the hrgr cDNA. Positive clones were grown up and maxiprep purified (Qiagen). The purified plasmid cDNA inserts were then sequenced at the Core Sequencing Facility NYU Medical Center.

Northern Analysis

RNA was isolated with the Trizol reagent and protocol (Gibco). Northern blotting was performed using agarose-formaldehyde gels (Ausubel et al., 1987). Probes were labeled with $^{32}$P-dCTP using the Redi-Prime random priming kit (Amersham). Transfers were made to nylon membranes (Amersham) and the membranes were exposed to UV radiation in a transilluminator for 10 minutes for crosslinking. Filters were hybridized overnight at 42° C. in hybridization solution containing 50% formamide. Final washes were for 15 minutes at 55° C., in 0.1×SSC and 0.1% SDS.

RACE Reactions

Several types of PACE reactions were utilized. The first was the standard reaction (Clontech, Palo Alto, Calif.). This reaction utilizes a reverse transcription reaction primed with a poly dT primer. The resulting single stranded cDNA is copied with an enzyme cocktail containing DNA Pol I, RNase H and DNA ligase. DNA adaptors are then ligated to the ends of the cDNA. PCR amplification can then be performed using a gene specific primer and an adaptor primer. To amplify full-length 5' ends the GeneRacer technique was used (Invitrogen, Carlsbad, Calif.; Ambion, Austin, Tex.). This technique only utilizes RNA, which is phosphorylated on the 5' end to eliminate all uncapped RNA fragments. Next, mRNA caps were removed using tobacco alkaline phosphatase freeing 5' phosphate groups from mRNA that was capped, and therefore full length. The third type of RACE used was the GENEWALKER (Clontech). This technique was used to walk along genomic DNA, amplifying from a known region to an unknown one. The basis of this technique is to digest the genomic DNA at specific sites using blunt end producing restriction enzymes and then ligating DNA adaptors. The known sequence was then extended with standard PCR. The products of all RACE reactions were subcloned into the PCR2.1 vector (Invitrogen).

PCR Assay to Detect Abnormal Transcripts

The forward primer was 5'-ATGACGGTGAGAA-CAACGGCAACAG CTACAGG-3' (SEQ ID NO:3) corresponding to sequences in exon 8B (normally intronic) and therefore not included in the sequence of FIG. 1. The reverse primer sequence was 5'-CGGGTTTTCGGGCTC CAGCTG-GCAGG-3' (SEQ ID NO:4) located in exon 13 and its boundaries are 1349-1419.

Results

Identification of the Human rgr Orthologue

To determine if the rgr gene is involved in human cancer, the present inventors decided to identify its human orthologue (hrgr). The GCG program BLAST was first utilized and a search was conducted for human sequences homologous to the rabbit rgr (GenBank accession no. U82163 and designated as oncogene rsc because it is a fusion between rgr and another sequence, where the rgr sequence of 1,707 nucleotides is from nucleotides 800 to the end). Two sequences, one corresponding to a genomic sequence and the second corresponding to a 112 bp EST sequence, were identified to be isolated from the mRNA of the human Jurkat cell line.

When these two sequences were compared with the rabbit rgr cDNA, although they did not contain any significant overlapping regions with each other, they were homologous to different regions of the rabbit gene. To further characterize these products, additional DNA sequences were obtained after extension using various RACE strategies. The extension by RACE of the EST sequence, performed using mRNA from Jurkat cells, allowed for the identification of a shortened cDNA when compared to the rabbit cDNA. Nevertheless, this human cDNA contained a 5' ATG starting codon with an appropriate open reading frame encoding a putative polypeptide with an approximate expected molecular weight of 22 KD. Upstream genomic sequences contained the other EST and had high homology to the 5' portion of the rabbit rgr gene. A complete sequence of the full-length cDNA for the human rgr gene is presented in FIG. 1.

Northern analysis showed that Jurkat cells expressed the hrgr gene at very high levels, but the transcript was much shorter than predicted by examining the hypothesized exons and by the size of the rabbit rgr cDNA (FIG. 2A). In addition, when an identical Northern was probed with the 5' homologous hrgr sequence, no hybridization was seen with Jurkat mRNA (FIG. 2B). These observations led us to hypothesize that the hrgr transcripts from the Jurkat cells might not contain the 5' region of the transcript.

Identification and Analysis of the Full-Length Normal hrgr Sequence

Three full-length hrgr sequences were isolated from a testis library. The sequences contained all of the hypothesized exons in addition to the nucleotide sequences found in the Jurkat cDNA (FIG. 1). The map shows the intron/exon junctions and the amino acid sequence. The amino acid sequence is highly homologous to the RalGDS family of proteins. The comparison of the amino acid sequence of the hrgr with those of rabbit rgr and other RalGDS family members showed that the family member with the highest homology to hrgr was rgr, indicating that hrgr is in fact the orthologue of rabbit rgr. In addition, using the GCG program BLAST, hrgr is the human gene with the highest similarity to the rabbit rgr gene in the human database. The homology of hrgr with the RalGDS family of proteins runs through the whole coding region starting at −440 in FIG. 1. The only region without homology to the RalGDS family is the shaded area in FIG. 1, which may be an intron since, although it was not excised in the transcripts isolated from the cDNA libraries. The location of the hrgr gene was found to be at chromosomal position 22q11.2. This could be of significance because translocations at this location are frequently seen in human tumors.

The Tumorigenicity of the Jurkat hrgr Transcript

Figure 6:
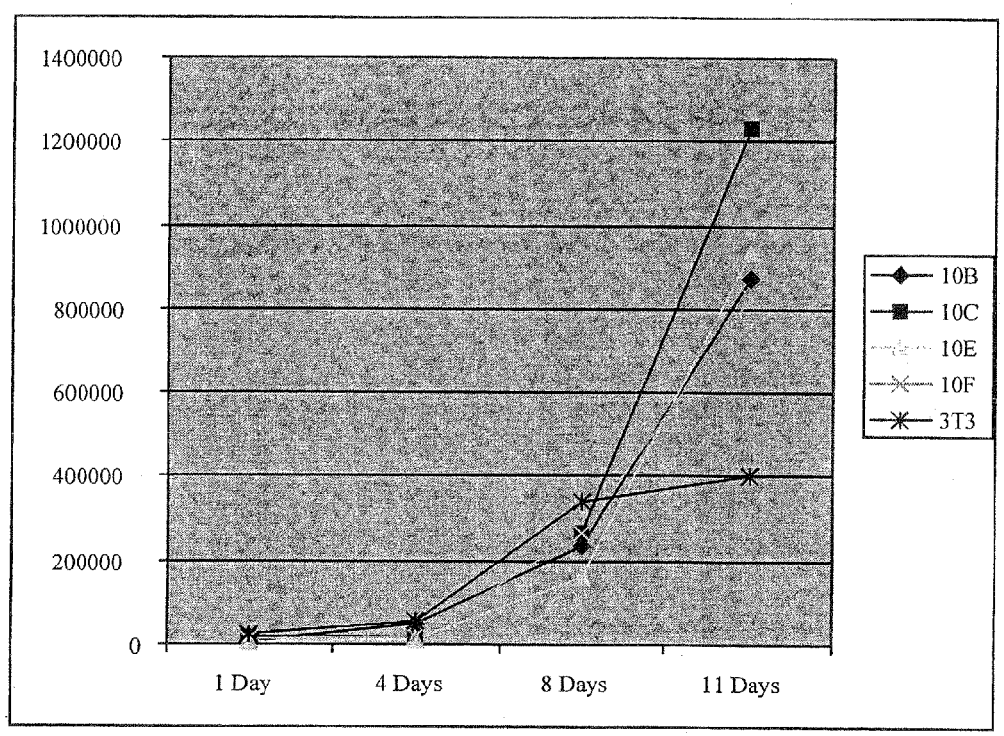
FIG. 6 is a graph of the number of cells from each cell line versus time (in days) showing that 3T3 cells, transfected with the Jurkat truncated hrgr, are transformed. Cell lines 10B, 10C, 10E, and 10F are 3T3 cells transfected with the truncated Jurkat transcript 10B in the eukaryotic expression vector PCR 3.1. Those cells and 3T3 cells transfected with the empty vector were grown on low serum media (1%). Each cell line was plated in triplicate with an equal number of cells.

A significant difference between the transcripts from the Jurkat cell line and the normal transcript, besides the lack of the 5' end, is that Jurkat transcripts contain a 5' exonic sequence that is intronic in the normal transcripts. This additional sequence contains a start codon that maintains the same reading frame present in normal transcripts (FIGS. 3 and 4) and allows the truncated Jurkat transcripts to be translated. To determine if the truncated transcript present in Jurkat cells has transforming potential, the laboratory of the present inventors made several eukaryotic expression constructs with the truncated Jurkat transcripts and the normal hrgr transcripts isolated from mRNA of human testes (FIG. 3). NIH3T3 cells transfected with the Jurkat constructs were found to have a transformed phenotype (FIGS. 5A-5D) and they were able to grow in the soft agar assay (FIGS. 5E-5H). Additionally, the clones expressing the truncated Jurkat hrgr transcripts could also grow in low serum (1%) (FIG. 6). Cells transfected with the full-length hrgr cDNA acquired none of these properties.

The Detection of Several hrgr Splicing Variants

Figure 4:
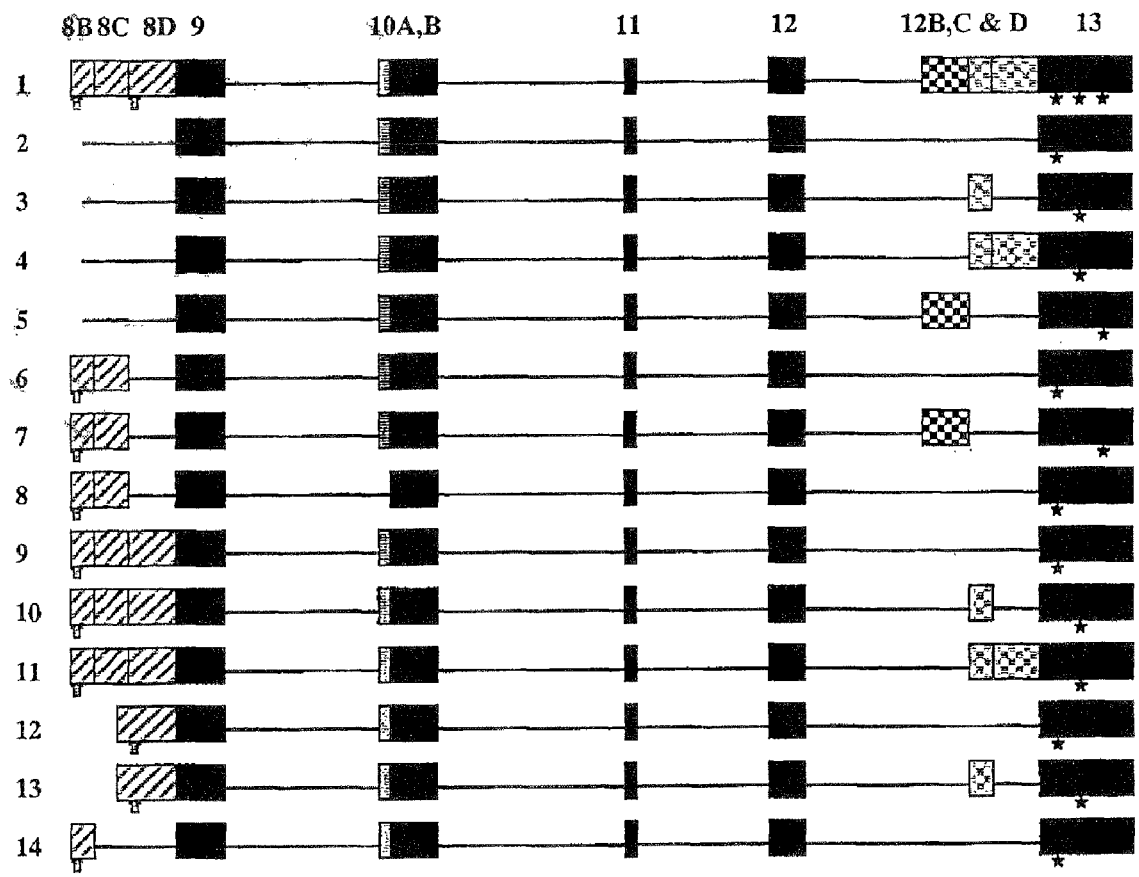
FIG. 4 schematically illustrates that the 3' region of the hrgr transcripts shows alternative splicing and abnormal exons in the truncated transcripts. Several different 3' cDNA sequences have been isolated and sequenced. The presence of additional exons between exon 8 and exon 9 (designated exons 8B, 8C and 8D) is restricted to tumor cell lines. Exon map 1 shows all possible exons and it has not been observed yet. The presence of exons 8B, 8C and/or 8D will change the start codon, but it will not change the reading frame for the remainder of the transcript. The addition of the variable exons 12B, 12C or 12CD does change the reading frame for the final exon 13 and in doing so it changes the stop codon. Schemes 2, 3 and 4 were observed and sequenced from a human testis library. Schemes 2 and 4 were observed and sequenced from human liver mRNA. All of the remaining variants were observed in the Jurkat cell line except variant 8 which was only seen in the Karpas cell line. Several of the truncated variations were seen in either the Karpas or the DHL cell lines. The dark and light colored exons are present in all normal transcripts analyzed. The striped exons are present only in abnormal transcripts from tumor cells. The checkered exons are alternative splicing variants. The darkly checkered exons make the transcript use the last stop codon, while the lightly checkered exons make the transcript stop in the middle stop codon. The stars represent the position of the different stop codons used by the different transcripts.
Figure 5A:
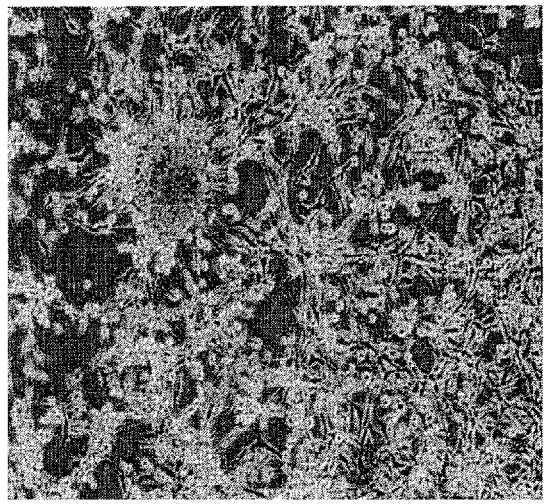
FIGS. 5A-5H show that 3T3 cells transfected with the Jurkat truncated hrgr are transformed. 10B (FIG. 5A), 10C (FIG. 5B), and 10E (FIG. 5C) are 3T3 cell lines transfected with the eukaryotic expression vector PCR3.1 containing truncated hrgr as an insert.
Figure 5B:
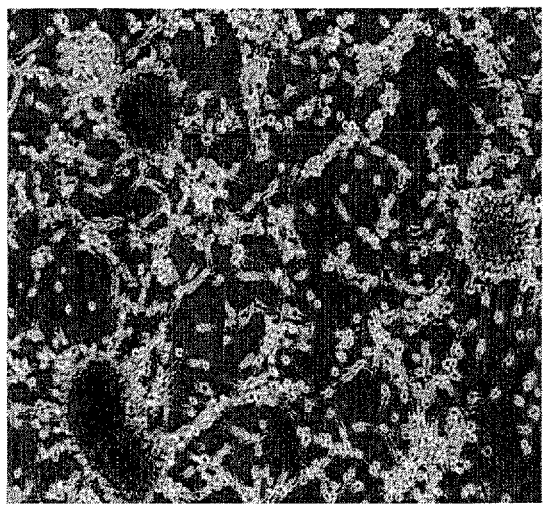
Figure 5C:
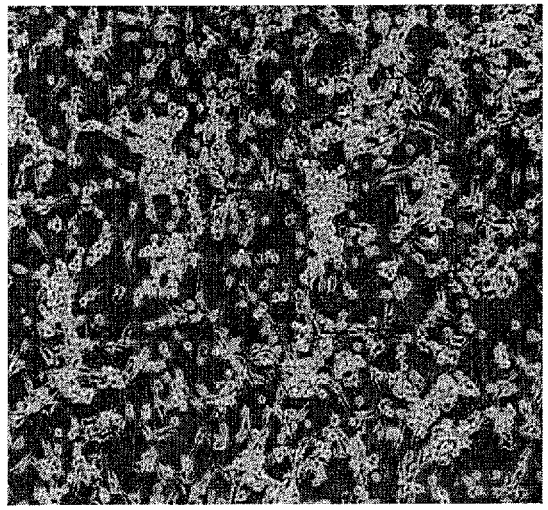
Figure 5D:
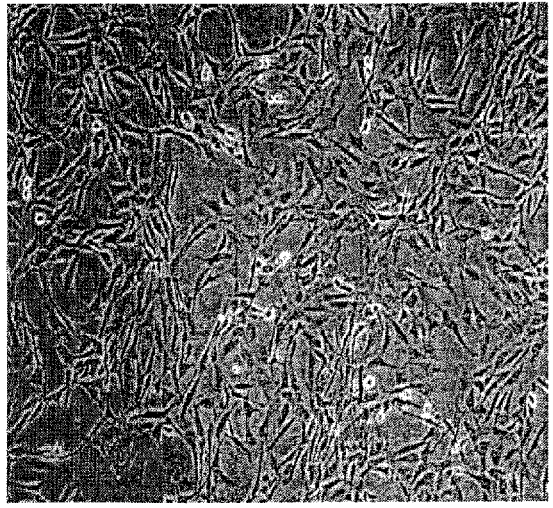
Figure 5E:
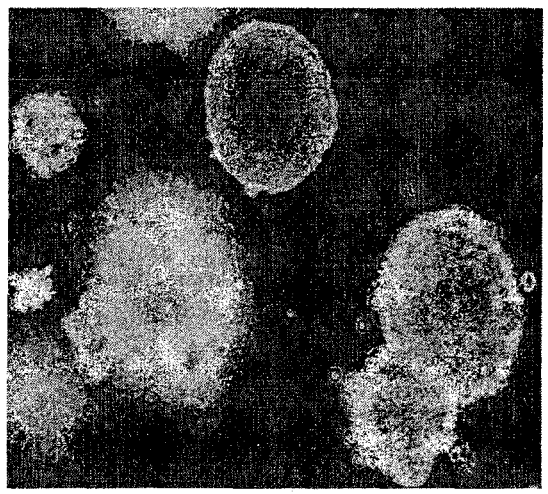
Figure 5F:
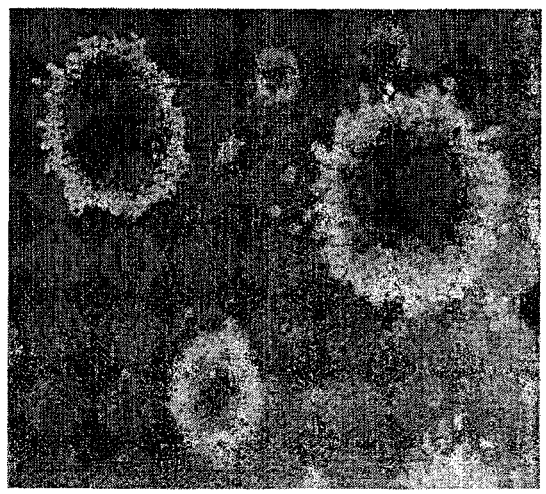
Figure 5G:
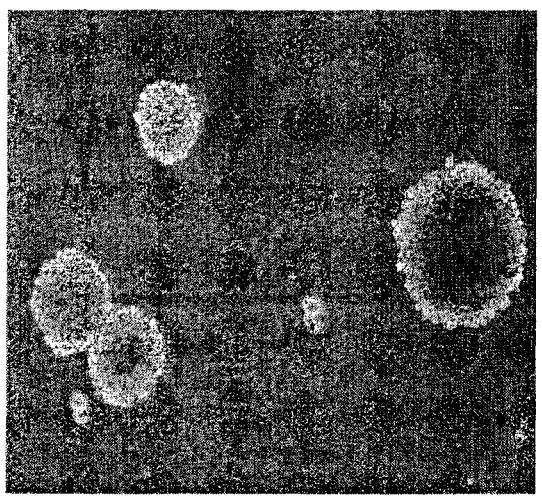
Figure 5H:
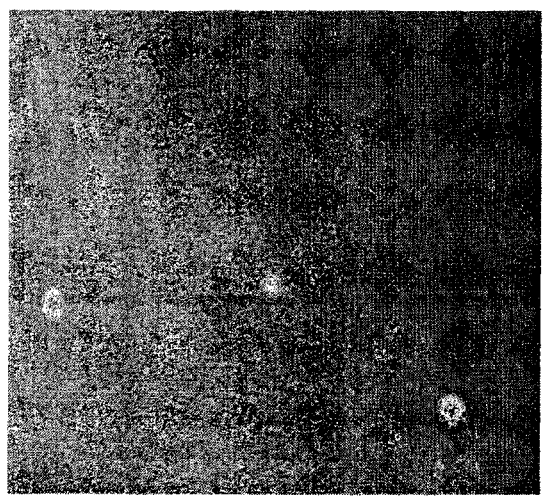

Sequencing analysis of multiple truncated and normal hrgr cDNAs showed that the 3' region of the gene could be represented by numerous splice variants in both the normal and truncated gene products (FIGS. 3 and 4). Interestingly, in almost all cases the reading frame was maintained. The exception to this was that some transcripts presented additional exonic sequences between the 12 and 13 exons. Depending on the presence or absence of these additional exons, different reading frames were used in exon 13 (FIG. 4). The presence or absence of these exonic sequences provides a significant degree of diversity in amino acid sequence, translation stop codons, and therefore, protein size. Additional exonic sequences between the 8 and 9 exons were also seen only in the abnormal transcripts from tumor cells (FIGS. 3 and 4). The presence of these exonic sequences allows for the addition of a start codon, which maintains the reading frame of the normal protein. Because all these abnormal transcripts have additional 5' exonic sequences not present in the full-length normal transcripts, it is possible to screen for the abnormal transcripts by looking for the presence of these new exonic sequences in transcripts from cell lines and tissues. This was done using RT PCR with primers whose location is shown with an asterisk in FIG. 3.

Using this approach, the RNA from several human cell lines and human tissue samples from either normal individuals or patients with T and B cell malignancies were screened (Table 1). DNA sequencing of the PCR products derived from neoplastic samples confirmed the specificity of the products and documented the presence of 5' exonic sequences of the hrgr gene within these abnormal transcripts. As shown in Table 1 all normal lymphoid tissue samples were negative. Several human cell lines derived from T cell malignancies were positive (CEM, DHL, Karpas and Jurkat). None of the B cell lymphomas was positive, while a number of fresh samples derived from T cell malignancies scored positive (see Table 1). It is important to emphasize that a number of the positive samples were derived from Peripheral T Cell Lymphoma (PTCL) patients. The present inventors therefore propose that the hrgr gene may be involved in the pathogenesis of some T cell lymphomas.

TABLE 1

Presence of abnormal hrgr transcript

| Diagnosis[1] | Number | Immunophenotype | Positivity |
|---|---|---|---|
| MF[2] | 7 | T-cell | 2/7 |
| PTCL[2] | 11 | T-cell | 9/11 |
| AILD[2] | 3 | T-cell | 0/3 |
| ALL[2] | 1 | T-cell | 0/1 |
| ATLL[2] | 1 | T-cell | 0/1 |
| ALCL-ALK+[2] | 5 | T-cell | 2/5 |
| EBV-LCL[3] | 6 | B-cell | 0/6 |
| Burkitt's lines[3] | 6 | B-cell | 0/6 |
| HCL[3] | 2 | B-cell | 0/2 |
| ALCL-ALK+ lines[3] | 3 | T-cell | 2/3 |
| T-LCL[3] | 2 | T-cell | 2/2 |
| Normal T cells[4] | 3 | T-cell | 0/3 |
| Thymus[4] | 3 | T-cell | 0/3 |
| Spleen[4] | 3 | B/T cell | 0/3 |
| Tonsil[4] | 3 | B/T cell | 0/3 |
| Liver[4] | 1 | N/A | 0/1 |

[1]Abbreviations used: Mycosis Fungoide (MF); Peripheral T-Cell Lymphoma (PTCL); Angioimmunoblastic Lymphadenopathy (AILD); Acute Lymphoblastic Leukemia (ALL); Adult T-Cell Leukemia/Lymphoma (ATLL); Anaplastic Large Cell Lymphoma (ALCL); Epstein-Barr Virus-Lymphoblastic Cell Line (EBV-LCL); Hairy Cell Line (HCL); T-Cell Lymphoma Cell Line (T-LCL).
[2]Samples used were derived from patients.
[3]Samples used were derived from cell lines.
[4]Samples used were derived from normal tissue.

Figure 7:
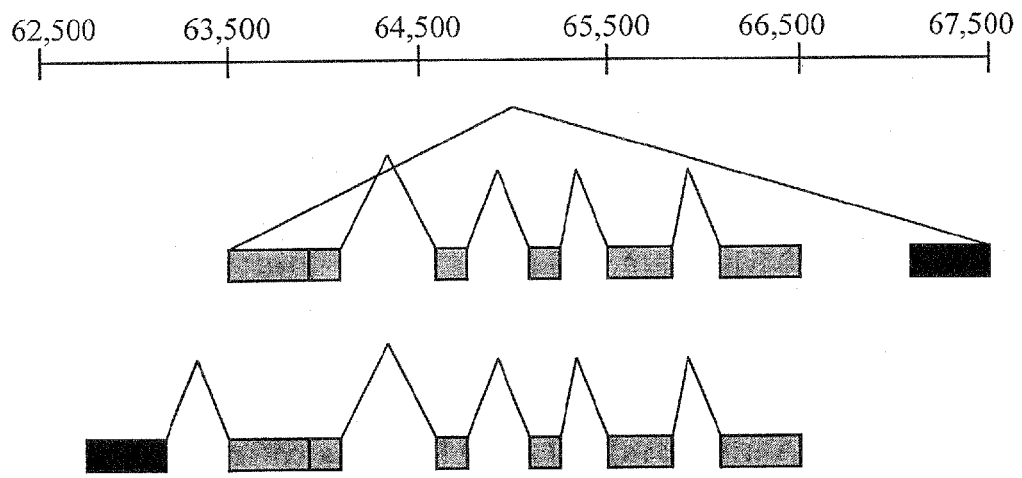
FIG. 7 schematically shows that the sequence of the hrgr transcript in DHL cells indicates that the DNA containing the 3' portion of the hrgr gene has undergone a rearrangement. As illustrated in this figure, the 3' genomic DNA sequence in black was found to be rearranged as the 5' end of the truncated hrgr transcript from DHL cells.

To further investigate the pathogenic mechanisms leading to generation of the hrgr truncated transcripts, Southern blotting analyses of Jurkat and other T cell lines that were positive for the abnormal transcript by RT PCR were performed. By comparing the pattern profiles of normal genomic DNA with those of Jurkat, the present inventors found that the hrgr bands from CEM and DHL appear to migrate at a slightly different mobility with two restriction enzymes, but the results were inconclusive (data not shown). As an alternative, to determine the molecular mechanism of activation of the abnormal hrgr transcripts, the GENERACER technique was used to analyze the 5' region of the DHL cell line hrgr transcript. Using this approach, it was demonstrated that the PCR derived band of DHL had a different molecular weight when compared to the products of Jurkat or normal human cDNAs. The laboratory of the present inventors found after subcloning and DNA sequencing that the DHL GENERACER RT-PCR product contained sequences in its 5' region, which corresponded to residues normally present within the 3' region of the hrgr gene (FIG. 7). The rearranged sequence does not involve coding regions (the start codon is the same for the DHL and Jurkat transcripts). Nevertheless, it indicates that the genetic event responsible for the production of the abnormal transcript in DHL cells is a genetic rearrangement that allows abnormal exonic sequences to be used, producing a truncated transcript (FIG. 7). This could explain why in this cell line the truncated transcript is made. Further analysis should determine if this type of rearrangement is seen in other cell lines and tumor tissues that express the truncated transcript.

Rgr-Induced Tumor Development in Transgenic Mice

To determine the in vivo oncogenic potential of rgr, its cDNA was used as a transgene to produce transgenic mouse lines under different promoters: 1) the constitutive promoter from murine sarcoma virus (MSV), which is expressed at significant levels in a wide range of tissues; 2) the chicken β-actin promoter with the cytomegalovirus enhancer, which is expressed ubiquitously starting at the 4-cell stage in embryonic development; and 3) the modified CD4 promoter, which consists of the CD4 minimal promoter, lacking the CD8 silencer region, but containing the CD4 enhancer to drive expression in CD4 and CD8 positive T cells (both single and double positives) (Ellmeier et al., 1997).

The MSV-Rgr construct produced a total of 66 mice, 16 of them positive for the transgene. Five lines that express it were expanded. All lines appear to have a similar phenotype with expression in the brain, eye, muscle and testis and two of them (lines 21 and 43) were studied in detail. In these two lines more than 95% of the mice showed cataracts concomitant with Harderian gland adenomas. Of those transgenic mice, 10% developed fibrosarcomas in the hind limbs and in the tail with a mean latency of 12 months and a range of 8 to 15 months (Table 2). Rgr is shown to be able to transform p15Ink4b deficient MEFs as efficiently as oncogenic Ras (Malumbres, et al., 2000). This indicates that absence of p15 cooperates with rgr. The MSV-Rgr mice was crossed with p15Ink4b null mice to analyze in vivo cooperation. The transgenic mice with both genetic alterations develop the fibrosarcomas with a much shorter latency (3 to 12 weeks) (Table 2). These results indicate that the Rb pathway is involved in blocking the effects of Rgr.

Rgr Subcellular Localization

The N-terminus of the oncogenic Rgr was tagged with GFP, NIH 3T3 cells were transfected, and stable clones were selected. The levels of rgr expression in the different transfectants by Northern blot were analyzed and Rgr subcellular localization in living cells was observed by epifluorescence microscopy. The clones that exhibit low expression of GFP-Rgr present a normal morphology. However, the clones that overexpress the fusion protein show a transformed morphology (Hernandez-Munoz, et al., 2003). These experiments support the notion that Rgr needs to be overexpressed and that the GFP fusion proteins are functional and transforming when overexpressed. The present inventors propose to further analyze the oncogenic mechanisms elicited by rgr using confocal microscopy localization of the protein and its possible co-localization with Ras or its effectors. An example of such

TABLE 2

INCIDENCE AND LATENCY OF DIFFERENT TUMOR TYPES IN RGR-TRANSGENIC MICE

| Transgenic mice | Phenotypes | Incidence | Latency |
| --- | --- | --- | --- |
| MSV-RGR | Inherited cataracts of the lens | >95% | Since birth |
| | Harderian gland adenomas | Concomitant with cataracts | |
| | Fibrosarcomas (hindlimbs and tail) | 10% | Average: 12 months |
| | | | Interval: (8-15 months) |
| | Inguinal hernias in males | 90% (Line 43) & 5% (Line 21) | |
| MSV-RGR × Kop15 | Inherited cataracts of the lens | >95% | Since birth |
| | Harderian gland adenomas | Concomitant with cataracts | |
| | Fibrosarcomas (hindlimbs and tail) | 100% | 3-12 weeks |
| CMV-RGR | Lethal embryonic | — | — |
| CD4-RGR | Malignant Thymic Lymphoma | 83% (Line 19), 36% (Line 37) & 60% (Line 42) | Averages: 22, 28, 17 weeks |
| | | | Intervals: (10-53)(15-43)(9-24) |

2) The actin-CMV-Rgr construct appears to be lethal embryonic, probably from the early expression of the transgene, since after three injections and 40 mice born, none of them were positive for the transgene.

3) The CD4-Rgr transgenic study was more recently initiated when we had indications that rgr was activated in human lymphomas. 16 transgenic mice out of 57 born were obtained, of which three lines display significant incidence of lymphomas (lines 19, 37 and 42, Table 2). In line 19, 83% of the transgenic mice have developed thymic lymphomas (FIG. 8) with a median latency of 22 weeks and a range of 10 to 53 weeks. These results are very encouraging and indicate that rgr has a significant ability to induce lymphomas in vivo.

Construction of a Rgr Dominant Negative Mutant (DNM)

Figure 11A:
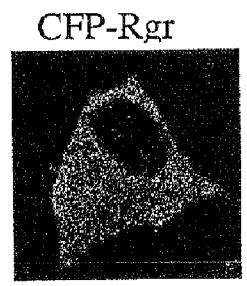
FIGS. 11A-11C are epifluorescence images showing that rgr is located in the cytosol and activates both H-ras and N-ras in the plasma membrane and Golgi.
Figure 11B:
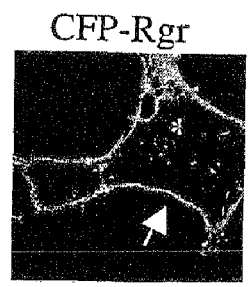
Figure 11C:
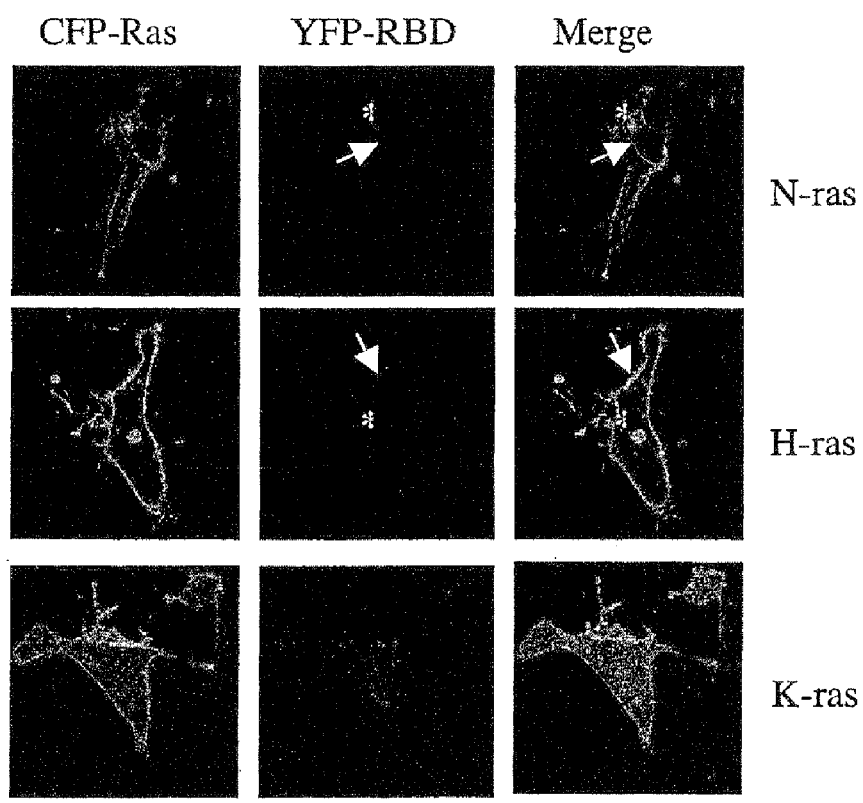

Point mutants in the catalytic domain are unable to transform NIH3T3 cells and they have been used to try to inhibit the rgr oncogene. Fixed amounts of the oncogene was transfected into NIH 3T3 with increasing amounts of the point mutant in the catalytic domain and the expression of SRE-luciferase as readout. Five times more point mutant than oncogene significantly reduced the luciferase activity induced by the oncogene (FIG. 9). In addition, since Ras activation is one of the main pathways that rgr uses to induce transformation, the effectiveness of the rgr-DNM to block Ras or Ral activation induced by the oncogene was analyzed. In FIG. 10, transient expression of the DNM in the presence of the oncogene and the RBD binding method were used to measure the level of Ras or Ral activation. The expression of the dominant negative mutant (5 times) is able to significantly block Ras and Ral activation elicited by the rgr oncogene, and therefore it supports the notion of the competing effect of this mutant and its usefulness to block rgr oncogenic effects.

an experiment in FIG. 11A shows that Rgr is normally cytoplasmic, while it moves to the Golgi and the plasma membrane in the presence of Ras (FIG. 11B), supporting the notion of rgr activation of Ras. Moreover, using the different Ras isoforms labeled with CFP and the RBD fragment of Raf labeled with YFP in COS cells in the presence of Rgr is shown in FIG. 11C. The results indicate that in the presence of Rgr activation of H-ras and N-ras occurs, but not K-ras. This activation occurs at the plasma membrane and at the Golgi apparatus.

Role of Rgr in Human Lymphomas

To determine if rgr is involved in human cancer, its human orthologue (hrgr) was isolated. Using the rabbit sequences, the human databases were searched. ESTs with significant homology had been isolated from Jurkat cells and the present inventors observed in these cells a transcript with strong hybridization but shorter than predicted from the size of rabbit rgr. Cloning and sequencing of this transcript showed a truncated form of rgr. The search of the human genomic database identified putative upstream exons that were not present in the Jurkat transcript. Isolation of transcripts from testes cDNA libraries produced several transcripts with 13 exons and coding a protein of 473 amino acids. The transcripts from Jurkat cells lacked the first 8 exons and elimination of 5' sequences repressing translation is shown to be a mechanism for rgr activation. These truncated transcripts were cloned in expression vectors and transfected into NIH 3T3 cells. The Jurkat transcripts were able to induce transformed morphology, growth in low serum and anchorage independence indicating that they indeed were oncogenic.

Figure 12A:
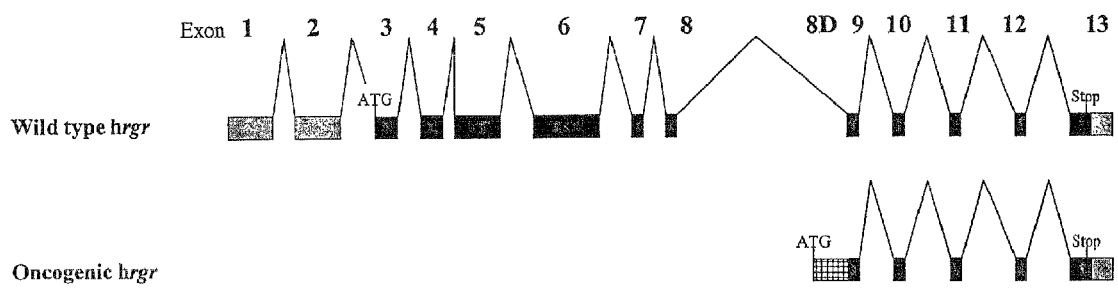
FIGS. 12A and 12B schematically illustrate the genomic organization of the human (FIG. 12A) and rabbit (FIG. 12B) rgr genes. Exons are presented as boxes, coding regions are solid, and the 5' UTR (containing uORF in the rabbit) and the 3' UTR of the transcripts are open. Introns are drawn as lines. Grilled boxes indicate coding sequences that are only present in the oncogenic forms being intronic sequences in the wild type genes. Asterisks indicate the exon location in which mutations were made to obtain dominant negative forms of rgr (D2A.1 and D2B.1).
Figure 12B:
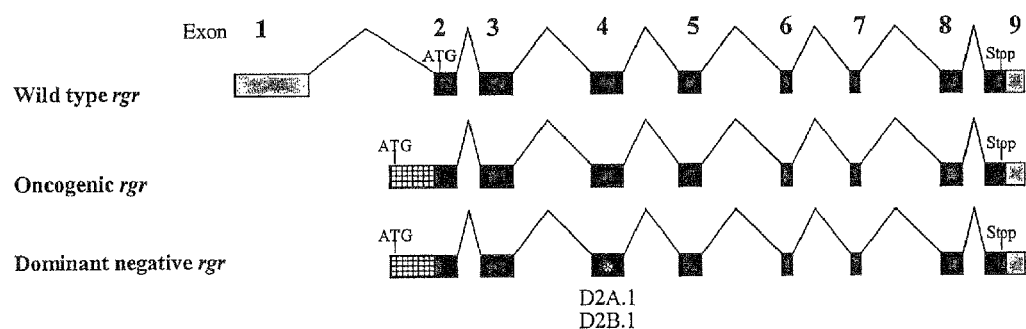

Those transcripts had acquired at the 5' end sequences from intron 8 that were now exonic and provided an initiation codon in frame with the rest of the protein that kept the normal reading frame (FIGS. 12A and 12B). These sequences from intron 8, specific for the aberrant transcript, were used to make a PCR primer to screen human lymphoma cell lines. Six B-lymphoblastoid cell lines and 6 Burkitt cell lines were negative, as were 2 lines from Hairy cell leukemia. In contrast, 2 out of 3 cell lines from anaplastic large cell lymphoma ALK+ (ALCL) were positive for the aberrant transcript (Karpas, 299 and DHL) as well as two other T cell lymphoma lines. Primary human samples were screened by the same assay. All samples from normal T cells, thymus, spleen, tonsil and liver were negative, as well as samples from angioimmunoblastic lymphadenopathy, acute lymphoblastic leukemia and adult T cell leukemia. In contrast, 2 out of 5 samples from ALCL ALK+, 2 out of 7 samples of mycosis fungoides and 9 out of 11 samples of peripheral T cell lymphomas (PTCL) were positive for the aberrant transcript. These results strongly implicate hrgr in the pathogenesis of several T cell malignancies and particularly in PTCLs.

sRNAi Inhibition of Rgr

Figure 13A:
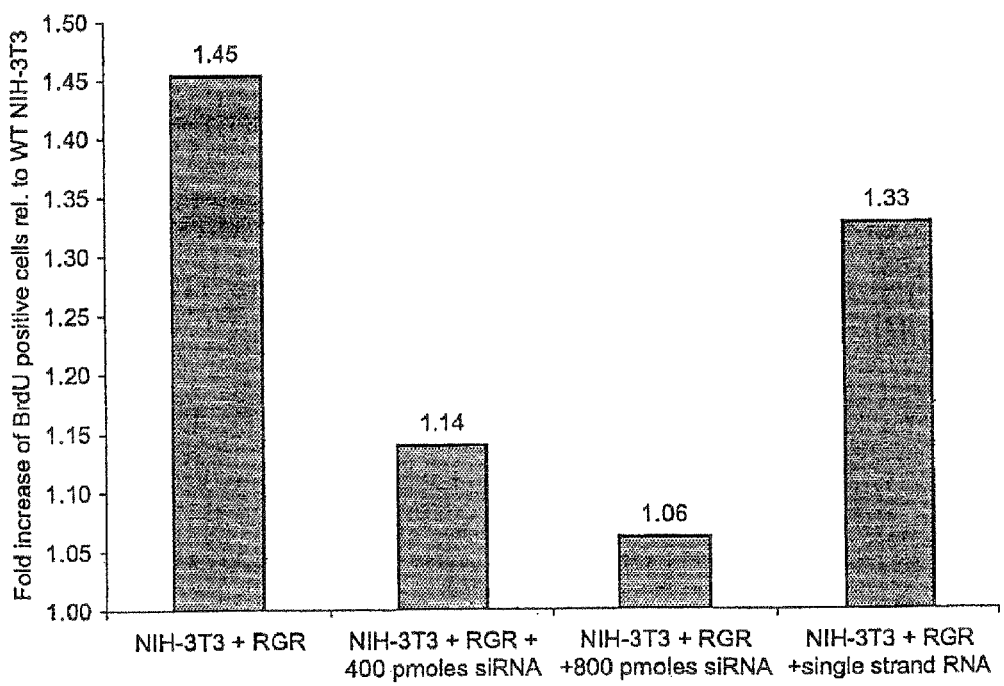
FIGS. 13A and 13B are graphs showing suppression of Rgr expression using RNAi.
Figure 13B:
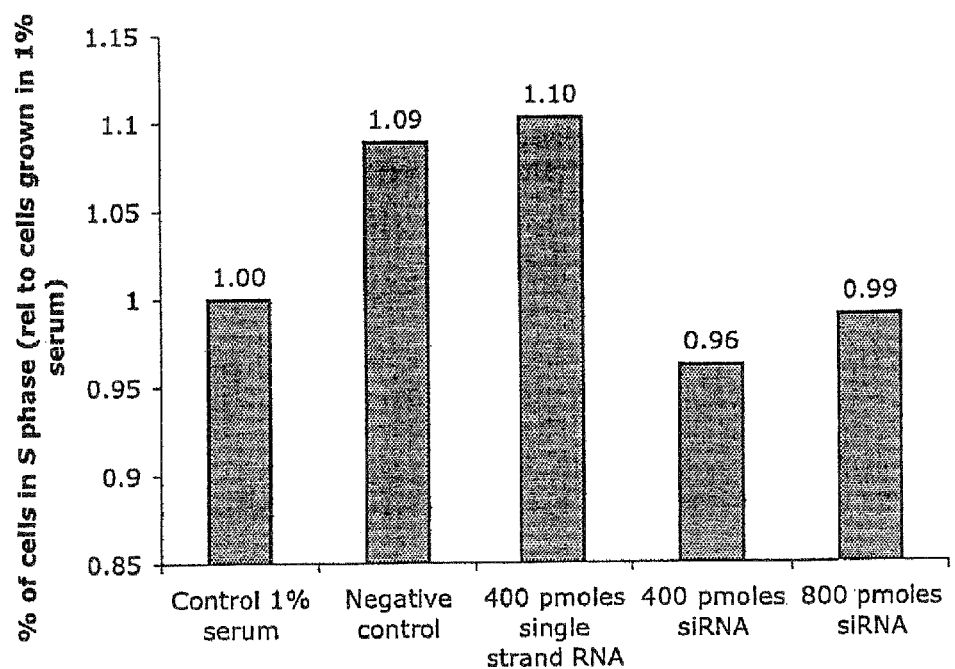

The effect of sRNAi in reducing the effects of the rgr oncogene in NIH3T3 cells was investigated. The databases were searched for sequences in rgr that had low probability of interfering with another gene in the mouse database. A 22 nucleotide sequence located starting at position 741 from the AUG was chosen as the target sequence. Its G:C content is 47.6%. To target that sequence, a sense strand RNA (SEQ ID NO:25) and an antisense strand (SEQ ID NO:26) were synthesized. Rgr-transformed NIH3T3 cells were transformed, and the next day either nothing as a control or the single strand RNA or the sRNAi at two different concentrations (400 and 800 pmoles) was added. The readout was BrdU incorporation after three treatments with the sRNAi. The results presented in FIG. 13A indicate that the control single strand RNA produced only a slight decrease of BrdU incorporation versus the untreated rgr-NIH3T3 cells. By contrast, the sRNAi produced a substantial reduction that was more pronounced with a higher concentration. This indicates that this gene is amenable to inhibition by sRNAi. Moreover, the experiments were initiated to use sRNAi in Jurkat cells. The sense and antisense RNA sequences, SEQ ID NOs:27 and 28 respectively, which were taken from exon 12 of the human rgr gene, were synthesized following the same conditions as above after searching the human database, and then three treatments of Jurkat cells grown in 10% serum at days 1, 2 and 3 with single strand as control and 400 and 800 pmoles of sRNAi were performed. The cells were measured for their fraction in S phase by PI content in flow cytometry at day 4. The results in FIG. 13B indicate that treatment with sRNAi was clearly inhibitory showing a fraction of cells in S phase even lower than the cells grown in 1% serum. This is a strong support for the notion that hrgr plays a role in the growth of Jurkat cells.

Expression Analysis of the Transcripts Modulated by Rgr

Experiments to determine the genes induced by the rabbit rgr oncogene were initiated to uncover what other pathways are activated by rgr (besides Ras and Ral). Different clones of NIH3T3 cells were used, some expressing rgr constitutively and others after induction by doxycycline. These RNAs have been compared with RNAs from NIH3T3 cells without rgr and with and without treatment with doxycycline, respectively. RNAs from rgr expressing cells were labeled with Cy5-dUTP, whereas those from control cells were labeled with Cy3-dUTP. Each pair of labeled probes was hybridized to a 27,000-element mouse cDNA chip. Images of each array were captured using an Axon scanner and the pixel intensities were determined using the Genepix 3.0 program. Global lowess normalization of signal intensities was performed using the R-package. After normalization, log base ratios were calculated for each chip and all genes were ranked by the mean log ratio. In Table 3, some of the genes involved in cell proliferation, cytoskeletal organization, signal transduction and apoptosis regulation that are modulated by the rgr oncogene were shown to be either upregulated at least by 2 times or down-regulated below 0.5 times in two independent experiments.

TABLE 3

| | Ratio |
|---|---|
| UP-REGULATED GENES | |
| Cell growth/proliferation and development/differentiation | |
| Megakaryocyte potentiating factor | 6.43 |
| Protein C receptor, endothelial | 2.88 |
| Glial cell line derived neurotrophic factor | 2.82 |
| Cytoskeletal organization/Cell adhesion | |
| Integrin alpha 6 | 3.18 |
| Syntrophin, basic 2 | 2.09 |
| Signal Transduction | |
| Mitogen-activated protein kinase 6 | 2.72 |
| RhoB gene | 2.66 |
| Urokinase plasminogen activator receptor | 2.43 |
| Serine/threonine kinase 10 | 2.23 |
| DOWN-REGULATED GENES | |
| Cell growth/proliferation and development/differentiation | |
| Pleiotrophin | 0.09 |
| Fibroblast growth factor receptor 2 | 0.28 |
| Osteoblast specific 1 | 0.29 |
| Growth arrest specific 1 | 0.32 |
| Platelet derived growth factor receptor, alpha polypeptide | 0.32 |
| Colony stimulating factor 1 (macrophage) | 0.38 |
| Cytoskeletal organization/Cell adhesion | |
| Microfibrillar associated protein 5 | 0.25 |
| Tissue inhibitor of metalloproteinase 3 | 0.27 |
| Procollagen, type V, alpha 2 | 0.29 |
| Procollagen, type XI, alpha 1 | 0.32 |
| Procollagen, type I, alpha 1 | 0.33 |
| Procollagen, type VI, alpha 1 | 0.37 |
| Procollagen, type III, alpha 1 | 0.40 |
| Immune function | |
| Complement component 1, r subcomponent | 0.25 |
| Lymphocyte antigen 6 complex | 0.29 |
| Cytotoxic T lymphocyte-associated protein 2 beta | 0.31 |
| Apoptosis regulators | |
| Thioredoxin interacting factor | 0.33 |
| Caspase 12 | 0.40 |

Analysis of the T Cells from Rgr-Transgenic Mice

The present inventors propose to analyze the lymphomagenic effects of rgr in vivo. For that purpose, the different stages of T cell development using four markers (CD44, CD25, CD4 and CD8) have to be analyzed. Different T cell populations in wild type mice and in one of the transgenic lines that contain the rgr oncogene driven by a CD4 modified promoter prior to their development of thymic lymphomas have been analyzed. The results compiled in FIG. 14 indicate that clear differences in the transgenic line versus the wild type mice can be detected. The activation of rgr in this system produces an increase in DN4 and double positives, while this results in a decrease of double negatives (due to a decrease in DN1 and DN2) and also a decrease in single positive CD4 thymocytes. In addition, full blown tumors were analyzed and they have a CD4 phenotype with high levels of expression of CD25 and a fraction of the cells expressing CD44 as well.

These experiments indicate that rgr expression in T cells results in a severe alteration of the patterns of differentiation and supports the notion that rgr plays a role in human lymphomas.

Quantitation of hrgr Transcripts

RNA expression levels of hrgr were quantitated using Real Time RT-PCR. Using this approach and primers specific for the abnormal transcript of hrgr (using sequences of exon 8D as primer) or for the wild type transcript (exon 3 primer), the expression levels of the two transcripts were determined in a number of normal tissues and tumor cell lines. These experiments have indicated that the normal transcript is only expressed in testes at measurable levels, but not in other normal or tumor tissues analyzed (including tonsils, spleen and B and T cells). By contrast, the abnormal transcript, although not expressed in any normal tissue analyzed is present in human lymphoma cell lines (FIGS. 15A and 15B), providing strong support that the abnormal transcript is indicative of pathology.

Discussion

Determination of the Nucleotide Sequence of the Human rgr Orthologue, hrgr

The goal of this study was to identify the human orthologue for rgr. To find the hrgr gene, the Genebank databases were first searched. One EST from Jurkat cells and one genomic sequence that had high levels of similarity with the rabbit gene were identified. When RACE was used to amplify the cDNA corresponding to the region of the genomic sequence that had been found in the database, the cDNA for this hypothesized transcript could not be found by RT PCR or Northern analysis using Jurkat cDNA. Since the laboratory of the present inventors had identified the rabbit rgr oncogene in a truncated form, the present inventors hypothesized that a similar process might have occurred in the Jurkat tumor cell line. The normal transcript from a human testis cDNA library was then isolated. From this library, three slightly different cDNA transcripts were isolated and sequenced. These transcripts were nearly identical to the hypothesized full-length sequence. This full-length cDNA sequence from testes varied from the truncated cDNA derived from Jurkat cells in two ways. First, it contained several 5' exons that were missing from the truncated sequences. Second, it lacked exonic sequences that the truncated transcripts have at their 5' ends. These abnormal exonic sequences afford the truncated transcripts a unique in frame start that is absent from the full-length sequence (FIGS. 3 and 4). We also identified the presence of the full-length sequence in human liver cDNA.

The Truncated hrgr Transcript is Oncogenic

The fact that the truncated transcripts, with the alternative start sites, were only found in the Jurkat tumor cell line and previous reports from the laboratory of the present inventors indicating that the rabbit rgr oncogene was also truncated led the present inventors to hypothesize that the truncation of the hrgr gene might also be oncogenic. The high levels of truncated hrgr observed in the Jurkat cells also hinted to the involvement of the gene in the Jurkat cell phenotype (FIG. 2A). To test this hypothesis, the biological activity of the Jurkat-derived cDNAs was compared with the full-length normal human transcript. It was found that the truncated transcripts were transforming when expressed in 3T3 cells while the full-length transcript was not. These results are consistent with the rabbit rgr results (D'Adamo et al., 1997) in demonstrating that the expression of this truncated transcript, rabbit or human, is in fact oncogenic. The oncogenicity of the truncated hrgr transcript present in Jurkat cells could be due to modified substrate specificity conferred by the truncation. In fact, as reported previously by the laboratory of the present inventors, a dominant negative ras mutant is able to block the malignant properties induced by a truncated rabbit rgr oncogene while a dominant negative Ral cannot (Hernandez et el., 2000). In addition, it is possible that the truncation has removed translational regulatory controls that facilitate the rgr expression (Hernandez et al., manuscript in preparation).

At the present time, only truncated hrgr EST sequences have been entered into the human database. Even more interesting is the fact that in all but one case the truncated hrgr EST sequence was isolated from a tumor source.

Development of an Assay to Detect the Abnormal hrgr Transcript

To detect the presence of the abnormal hrgr transcripts, the intronic sequences present in the 5' regions of the truncated transcripts were used to design primers for RT-PCR. The size of the sequences specific to the abnormal transcript (120-240 bp) is small, and the 5' sequences alone would be indistinguishable from genomic DNA using PCR amplification. To overcome this difficulty, 3' sequences within a region that is conserved in truncated and normal transcripts but separated from the 5'primer by introns (see FIGS. 3 and 4). Several ALCL lines that were positive for the truncated transcript were initially identified (Table 1). Upon analysis of a number of fresh tumors and cell lines, the laboratory of the present inventors found that B cell tumors, normal T-cells, tonsil, spleen, or thymus were negative for the abnormal transcript while several T cell lymphoid malignancies, including mycosis fungoides, ALCL and peripheral T cell lymphomas (PTCL) were positive. From these results, the present inventors propose that the expression of the truncated transcript is involved in the malignant phenotype of patients with a subset of T cell malignancies. It is notable that the very large majority of the PTCL analyzed so far carry these abnormal transcripts, suggesting that this tumor may represent a more homogeneous group of lymphomas than previously thought with possibly specific genetic lesions and or pathogenesis. Moreover, it would be extremely interesting to determine if the T cell malignancies, that contain these abnormal hrgr transcripts, might have a more aggressive course.

Genetic Events Responsible for the Expression of the Truncated hrgr Transcript

In normal human cells the expression level of the rgr gene is low, while the present inventors have observed that when transformed cells and tumor samples express the oncogene, the expression is significant. Analysis of the mRNA sequence of the truncated hrgr transcript from the Jurkat cell line revealed the sequence of the normal hrgr cDNA from exon 9 to the 3' end with the additional intronic sequences, now exonic, at the 5' end allowing its translation. The truncated transcript is then initiated at an alternative initiation site that normally falls in an intron. Following identification of other cell lines that expressed the alternative initiation exon using the RT PCR assay, the laboratory of the present inventors was unable to detect by Northern blot a similar transcript as the one observed in Jurkat cells (data not shown). Since they did however exhibit the alternative initiation exon, the present inventors hypothesized that these cell lines expressed a rearranged transcript. Analysis of the DHL cell line RNA confirmed this hypothesis since it contained the truncated hrgr sequence preceded by a 140 nucleotide sequence which in the normal genome is found 3' to the hrgr gene (FIG. 7). Therefore, the present inventors hypothesize that there are several mutational mechanisms that are utilized in different malignancies that result in expression of an abnormal hrgr transcript.

The Chromosomal Localization of the hrgr Gene

The chromosomal localization of the hrgr gene is to chromosome 22 at the position 22q11.2. The identification of the location of the hrgr gene together with the knowledge that its activation is associated with gene rearrangement, led the present inventors to investigate the frequency of such events in that region of the genome. The translocation present in the Philadelphia chromosome, which is postulated to be the main pathogenic factor in greater than 90% of CML and 30% of ALL (Chissoe et al., 1995), is localized 100 kb from the hrgr gene. This proximity provides support for the idea that this region of the genome is prone to rearrangements. It is also interesting to note that a BCR-like region exists immediately 5' of the hrgr gene. Translocation of the hrgr gene could produce its truncation and/or fusion genes, with the truncated hrgr transcript as a part of the fusion transcript. This could mimic the scenario observed in the rabbit (D'Adamo et al., 1997). The analysis in this example also demonstrates the presence of a novel immunoglobulin-like gene (Ig Lambda Chain C) within the hrgr gene (data not shown). It is well known that immunoglobulin genes undergo rearrangements particularly in lymphoid cells.

The present inventors also found evidence that in the region 5' of the hrgr coding region there are sequences that have a high level of similarity to exons 1-4 of the hrgr gene (greater than 81%) (data not shown) because this entire genomic region appears to be duplicated. This duplication only encompasses the 5' half of the hrgr gene. This indicates that at some point during evolution a duplication and rearrangement occurred of the hrgr gene or its ancestor. This is a similar type of event to what the present inventors postulate to be responsible for the production of the truncated hrgr transcript and activation of its oncogenic potential. The fact that translocation events frequently occur in the same place "hot spots" (Jiang et al., 1990) is consistent with the hypothesis that chromosomal rearrangements may be responsible for the production of the truncated hrgr transcript in human lymphomas.

In these experiments, the present inventors have been able to determine that truncation of a Ral exchange factor is able to endow the molecule with transforming capacity, but even more importantly the present inventors have been able to uncover several genetic mechanisms which can produce the abnormal transcript in human samples. Finally, oncogenic hrgr transcripts could be detected in a substantial fraction of human peripheral T cell lymphomas. These results therefore open the way for an additional diagnostic tool for the study of T cell lymphomas and for a better understanding of their pathogenesis.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Albright, C. F., Giddings, B. W., Liu, J., Vito, M. & Weinberg, R. A. *Embo J,* 12:339-47 (1993)

Ausubel, F. M., Brent, R., Kingston, R. E., Moore, D. D., Smith, J. A., Seidman, J. G., and Struhl, H. *Current Protocols in Molecular Biology*. John Wiley and Sons, Inc. New York, N.Y. (1987)

Better et al, "*Escherichia coli* secretion of an active chimeric antibody fragment", *Science* 240:1041-1043 (1988)

Bouck, N. & Di Mayorca, G. Methods Enzymol, 58:296-302 (1979)

Boulianne et al, "Production of functional chimeric mouse/human antibody", *Nature* 312:643-646 (1984)

Cabilly et al, "Generation of antibody activity from immunoglobulin polypeptide chains produced in *Escherichia coli*", *Proc Natl Acad Sci USA* 81:3273-3277 (1984)

Chissoe, S. L., Bodenteich, A., Wang, Y. F., Wang, Y. P., Burian, D., Clifton, S. W., Crabtree, J., Freeman, A., Iyer, K., Jian, L. & et al. *Genomics,* 27:67-82 (1995)

Colligan et al, *Current Protocols in Immunology*, Green Publishing Assoc., and Wiley Interscience, New York (2001)

D'Adamo, D. R., Novick, S., Kahn, J. M., Leonardi, P. & Pellicer, A. *Oncogene,* 14:1295-305 (1997)

Ellmeier, W., Sunshine, M. J., Losos, K., Hatam, F., and Littman, D. R. An enhancer that directs lineage-specific expression of CD8 in positively selected thymocytes and mature T cells, *Immunity.* 7:537-47, 1997

Eshhar et al, "Chimeric T cell receptor which incorporates the anti-tumour specificity of a monoclonal antibody with the cytolytic activity of T cells: a model system for immunotherapeutical approach", *Br J Cancer Suppl,* 10:27-29 (1990)

Gross et al, "Expression of immunoglobulin-T-cell receptor chimeric molecules as functional receptors with antibody-type specificity", *Proc Natl Acad Sci USA*, 86:10024-10028 (1989)

Harlow et al, *Antibodies: A Laboratory Manual*, Cold Spring Harbor Laboratory, Cold Spring Harbor, N.Y. (1988)

Hernandez-Munoz, I., Malumbres, M., Leonardi, P. & Pellicer, A. *Oncogene,* 19:2745-57 (2000)

Hernandez-Munoz et al., *Cancer Research* 63(14), Jul. 15, 2003

Jiang, X. Y., Trujillo, J. M. & Liang, J. C. *Blood,* 76:597-601 (1990)

Kohler et al, "Continuous cultures of fused cells secreting antibody of predefined specificity", *Nature* 256:495-497 (1975)

Leon, J., Kamino, H., Steinberg, J. J. & Pellicer, A. *Mol Cell Biol,* 8:786-93 (1988)

Liu et al, "Siah-1 mediates a novel beta-catenin degradation pathway linking p53 to the adenomatous polyposis coli protein", *Mol Cell* 7:927-936 (2001)

Malumbres, M., Perez De Castro, I., Hernandez, M. I., Jimenez, M., Corral, T., and Pellicer, A. Cellular response to oncogenic ras involves induction of the Cdk4 and Cdk6 inhibitor p15(INK4b), *Mol Cell Biol.* 20: 2915-25, 2000.

McManus, M. T. and Sharp, P. A., "Gene Silencing in Mammals by Small Interfering RNAs" *Nature Reviews Genetics* 3:737-747 (2002)

Morrison et al, "Chimeric human antibody molecules: mouse antigen-binding domains with human constant region domains". *Proc Natl Acad Sci USA* 81:6851-6855 (1984)

Neuberger et al, "A hapten-specific chimeric IgE antibody with human physiological effector function", *Nature* 314: 268-270 (1985)

Pellicer, A., Robins, D., Wold, B., Sweet, R., Jackson, J., Lowy, I., Roberts, J. M., Sim, G. K., Silverstein, S. & Axel, R. *Science,* 209:1414-22 (1980)

Sahagan et al, "A genetically engineered murine/human chimeric antibody retains specificity for human tumor-associated antigen" *J Immunol* 137:1066-1074 (1986)

Sun et al, "Chimeric antibody with human constant regions and mouse variable regions directed against carcinoma-associated antigen 17-1A", *Proc Natl Acad Sci USA* 84:214-218(1987)

White M. A., Vale, T., Camonis, J. H., Schaefer, E. & Wigler, M. H. *J Biol Chem,* 271:16439-42 (1996)

What is claimed is:

1. An isolated monoclonal antibody that binds to a polypeptide consisting of the amino acid sequence of SEQ ID NO:8.

2. A pharmaceutical composition comprising the monoclonal antibody of claim 1 and a pharmaceutically acceptable carrier, excipient, diluent, or auxiliary agent.

3. A method for diagnosing T cell malignancies associated with truncation of human Rgr protein, comprising:
    contacting a sample containing T cells obtained from a human subject with the monoclonal antibody of claim 1; detecting the presence or absence of binding of the monoclonal antibody of claim 1 to a truncated variant of human Rgr protein that comprises an epitope of SEQ ID NO: 8;
    diagnosing a T cell malignancy associated with truncation of human Rgr protein upon detecting the presence of binding between the monoclonal antibody of claim 1 and the truncated variant of human Rgr protein.

4. An isolated molecule having the antigen binding portion of a monoclonal antibody which binds to an epitope of SEQ ID NO: 8, wherein the antigen binding portion comprises the Fab fragment, the Fab' fragment, the F(ab')2 fragment, or the variable domains of the heavy and light chains of the monoclonal antibody.

5. A pharmaceutical composition comprising the molecule of claim 4 and a pharmaceutically acceptable carrier, excipient, diluent, or auxiliary agent.

6. A method for diagnosing T cell malignancies associated with truncation of human Rgr protein, comprising:
    contacting a sample containing T cells obtained from a human subject with the molecule of claim 4; detecting the presence or absence of binding of the molecule of claim 4 to a truncated variant of human Rgr protein that comprises an epitope of SEQ ID NO: 8;
    diagnosing a T cell malignancy associated with truncation of human Rgr protein upon detecting the presence of binding between the molecule of claim 4 and the truncated variant of human Rgr protein.

* * * * *

SEQUENCE LISTING

```
<160> NUMBER OF SEQ ID NOS: 28

<210> SEQ ID NO 1
<211> LENGTH: 2897
<212> TYPE: DNA
<213> ORGANISM: Homo sapiens
<220> FEATURE:
<221> NAME/KEY: CDS
<222> LOCATION: (1171)..(2589)

<400> SEQUENCE: 1
taaacccatc tcctcctatg ccacctgcct gggcccctcc tgggacttta tcactgtgcc      60
acactttttg gaactactgg ttagaaggtg agtgtccatc cccctccaag acacagaggt     120
gcctctgtcc cctactggct ctgtcttgaa gatgcacctc tcggagcctc ggttggctcc     180
tctggaacag ggagtagtga gaagacgaac ctcacagggt tcttgtaggg actcaatgat     240
ctaagacaca gcaaacaaag gggtccctag agcctaaaac tctggaaaat ctgctggggg     300
tgctgtgatt catgtttgtt acttttctct tccccctcac ttgaagcagc tctcagcatt     360
ctgcctcaat ggcctgtatc actcactgtt tggaaaaaca catagaaacc aagtctgcga     420
tggcactggt aaaggatgtc tgagattcct tctggctggt ctttctcctt gacacagaca     480
gaagaggggt cccttggtgc tgaaaaagga gccacaggcc cactcagaca tctggagagg     540
ctcactgggg ttctccaaag gttggggttc actcattcaa cacatacatt caaaacacct     600
catttgtgca tcgctcttct tggggcttgg cataatttca taaacaaagc agatgacaat     660
cccccggcct tgattctact cagagtcagg cactcacagt agacagaata aacaagtcat     720
atctacagaa tgttacaggt gagaccctca tggcctcctc tacgtatggt ggcatcctcc     780
cagattctga ctagaatgac gcagcccagc aacaaatata aactgggtgg atttagggtt     840
ctgaagggcc ttttcaccca caaacatggg ggaaaatat gtggactctg gctggggaga     900
gactaaagga gctctggggc tcatacttct tataattccc acgagaaggc tgacatctgg     960
ggacttcccc cacaagaggc aaatagtgag ttctgtaaat ggagacttag gtcccctgca    1020
```

```
aagcagaggg gaggctgggg tcacagctgg ccactgagag acccatcccc ctcagcaccg    1080
tggcttccca gctctccctg tcctcctccc cccgacatct gccccttccc tcctaacccc    1140
aggaccaggg gacccagatc tggagctttg atg agg aag ctg ctc aca aat ctg    1194
                                  Met Arg Lys Leu Leu Thr Asn Leu
                                  1               5 cct gca gct gca gtc ttg agt gcc cag gtg tac agt gct gtg ctc cag     1242
Pro Ala Ala Ala Val Leu Ser Ala Gln Val Tyr Ser Ala Val Leu Gln
    10              15                  20 ggc ctt tgg gaa gag aat gtc tgt ggg acg cca ggg cgc acg agg gtc     1290
Gly Leu Trp Glu Glu Asn Val Cys Gly Thr Pro Gly Arg Thr Arg Val
25              30                  35                  40 tgt aca gcc ctg ctg tat ggc cag gtc tgc ccc ttc cag gac agc act     1338
Cys Thr Ala Leu Leu Tyr Gly Gln Val Cys Pro Phe Gln Asp Ser Thr
                45                  50                  55 gat ggc tta cgc acc atc acc tcc att ttg ttc aac tgg ccc ccc gaa     1386
Asp Gly Leu Arg Thr Ile Thr Ser Ile Leu Phe Asn Trp Pro Pro Glu
                    60                  65                  70 aac act tca gtt tac tat cag ccc ccg caa cgg tca tct ttc cgg ata     1434
Asn Thr Ser Val Tyr Tyr Gln Pro Pro Gln Arg Ser Ser Phe Arg Ile
                        75                  80                  85 aag ctg gcc ttc agg aac ctc tcc tgg cct gga ctg ggc ttg gag gac     1482
Lys Leu Ala Phe Arg Asn Leu Ser Trp Pro Gly Leu Gly Leu Glu Asp
90                  95                  100 cat cag gaa att gtc cta ggc cag ttg gtg ctt ccg gag ccc aac gag     1530
His Gln Glu Ile Val Leu Gly Gln Leu Val Leu Pro Glu Pro Asn Glu
105                 110                 115                 120 gcc aag cca gat gat cct gct cca cgt cct ggg caa cac gca tta aca     1578
Ala Lys Pro Asp Asp Pro Ala Pro Arg Pro Gly Gln His Ala Leu Thr
                    125                 130                 135 atg ccg gcc ctg gag cca gca cca cca ctg ctg gcg gac ctg ggc cct     1626
Met Pro Ala Leu Glu Pro Ala Pro Pro Leu Leu Ala Asp Leu Gly Pro
                140                 145                 150 gct ctg gag cca gag tca cct gca gcc ctg ggt cca cca gga tat cta     1674
Ala Leu Glu Pro Glu Ser Pro Ala Ala Leu Gly Pro Pro Gly Tyr Leu
            155                 160                 165 cat tca gca cca ggg cca gca cca cca ggg gaa ggg ccc cct cca         1722
His Ser Ala Pro Gly Pro Ala Pro Pro Gly Glu Gly Pro Pro Pro
170                 175                 180 ggg aca gtg ctg gag cca cag tca gcc cca gag tcc tcc tgt ccc tgt     1770
Gly Thr Val Leu Glu Pro Gln Ser Ala Pro Glu Ser Ser Cys Pro Cys
185                 190                 195                 200 cgt ggg tct gta aag aac caa ccc agt gag gag ctg cct gac atg acg     1818
Arg Gly Ser Val Lys Asn Gln Pro Ser Glu Glu Leu Pro Asp Met Thr
                205                 210                 215 acc ttc cct ccc agg ctg ctg gca gag cag ctg acc ctc atg gat gcg     1866
Thr Phe Pro Pro Arg Leu Leu Ala Glu Gln Leu Thr Leu Met Asp Ala
                220                 225                 230 gag ctg ttc aag aag gtg gtc ctc cac gaa tgc ttg ggc tgc atc tgg     1914
Glu Leu Phe Lys Lys Val Val Leu His Glu Cys Leu Gly Cys Ile Trp
            235                 240                 245 ggc caa gga cat ctg aag ggg aat gag cac atg gca ccc aca gtt cgt     1962
Gly Gln Gly His Leu Lys Gly Asn Glu His Met Ala Pro Thr Val Arg
250                 255                 260 gcc acc atc gca cac ttc aac agg ctc acc aac tgc atc acc acc tcc     2010
Ala Thr Ile Ala His Phe Asn Arg Leu Thr Asn Cys Ile Thr Thr Ser
265                 270                 275                 280 tgc ctc ggg gac cac agc atg agg gcc cgg gac agg gcc agg gtg gtg     2058
Cys Leu Gly Asp His Ser Met Arg Ala Arg Asp Arg Ala Arg Val Val
                285                 290                 295
```

```
gag cac tgg atc aag gtg gcc agg gag tgc cta agc ctc aac aac ttc    2106
Glu His Trp Ile Lys Val Ala Arg Glu Cys Leu Ser Leu Asn Asn Phe
        300                 305                 310 tcc tcg gtg cac gtc atc gtc tct gct ctg tgc agc aac cca ata ggt    2154
Ser Ser Val His Val Ile Val Ser Ala Leu Cys Ser Asn Pro Ile Gly
            315                 320                 325 cag cta cac aag acg tgg gca gga gtg tcc agc aaa agc atg aaa gag    2202
Gln Leu His Lys Thr Trp Ala Gly Val Ser Ser Lys Ser Met Lys Glu
    330                 335                 340 cta aaa gaa ctc tgc aaa aaa gac act gca gtg aag agg gac cta ctg    2250
Leu Lys Glu Leu Cys Lys Lys Asp Thr Ala Val Lys Arg Asp Leu Leu
345                 350                 355                 360 atc aag gcg ggg agc ttt aag gtg gcc acc cag gag agg aac ccc cag    2298
Ile Lys Ala Gly Ser Phe Lys Val Ala Thr Gln Glu Arg Asn Pro Gln
                365                 370                 375 aga gtc cag atg agg ctg cgg agg cag aag aag ggt gtg gtc ccc ttc    2346
Arg Val Gln Met Arg Leu Arg Arg Gln Lys Lys Gly Val Val Pro Phe
            380                 385                 390 ctg ggg gat ttt ctg act gag tta cag agg ctg gat tcg gcc atc ccg    2394
Leu Gly Asp Phe Leu Thr Glu Leu Gln Arg Leu Asp Ser Ala Ile Pro
        395                 400                 405 gac gac ctg gat ggc aac acc aac aag agg agc aag gag gtc cga gtt    2442
Asp Asp Leu Asp Gly Asn Thr Asn Lys Arg Ser Lys Glu Val Arg Val
    410                 415                 420 ctg cag gaa atg cag ctg ctc caa gtg gct gcc atg aat tac agg ctt    2490
Leu Gln Glu Met Gln Leu Leu Gln Val Ala Ala Met Asn Tyr Arg Leu
425                 430                 435                 440 cgg cct ctt gag aaa ttt gtc acc tat ttc aca aga atg gag cag ctc    2538
Arg Pro Leu Glu Lys Phe Val Thr Tyr Phe Thr Arg Met Glu Gln Leu
                445                 450                 455 agt gac aaa gag agc tac aag ctg tcc tgc cag ctg gag ccc gaa aac    2586
Ser Asp Lys Glu Ser Tyr Lys Leu Ser Cys Gln Leu Glu Pro Glu Asn
            460                 465                 470 ccg taggctggca acatcctgca gtggctggga acccaccggg atgctggcca          2639
Pro gaacaccggc tctgcaccat ccctcaccca gaccgtagac accagggaac cacatctagg   2699
aggctggcag ctcagctgca tcttgccctg gatcctcatc accaactgct cctgctggcc   2759
aggatcaggc catgggactt tgtgagtca ggcgggagac catttatgt ttattttctt     2819 tagtgtataa gtaagggttt tttcttaact ttcgttaaaa taaaatttta aaaactatt    2879 caaaataaaa aaaaaaaa                                                 2897

<210> SEQ ID NO 2
<211> LENGTH: 473
<212> TYPE: PRT
<213> ORGANISM: Homo sapiens

<400> SEQUENCE: 2

Met Arg Lys Leu Leu Thr Asn Leu Pro Ala Ala Ala Val Leu Ser Ala
1               5                   10                  15

Gln Val Tyr Ser Ala Val Leu Gln Gly Leu Trp Glu Glu Asn Val Cys
            20                  25                  30

Gly Thr Pro Gly Arg Thr Arg Val Cys Thr Ala Leu Leu Tyr Gly Gln
        35                  40                  45

Val Cys Pro Phe Gln Asp Ser Thr Asp Gly Leu Arg Thr Ile Thr Ser
    50                  55                  60

Ile Leu Phe Asn Trp Pro Pro Glu Asn Thr Ser Val Tyr Tyr Gln Pro
```

-continued

```
              65                  70                  75                  80
Pro Gln Arg Ser Ser Phe Arg Ile Lys Leu Ala Phe Arg Asn Leu Ser
                    85                  90                  95
Trp Pro Gly Leu Gly Leu Glu Asp His Gln Glu Ile Val Leu Gly Gln
                    100                 105                 110
Leu Val Leu Pro Glu Pro Asn Glu Ala Lys Pro Asp Asp Pro Ala Pro
                    115                 120                 125
Arg Pro Gly Gln His Ala Leu Thr Met Pro Ala Leu Glu Pro Ala Pro
            130                 135                 140
Pro Leu Leu Ala Asp Leu Gly Pro Ala Leu Glu Pro Glu Ser Pro Ala
145                 150                 155                 160
Ala Leu Gly Pro Pro Gly Tyr Leu His Ser Ala Pro Gly Pro Ala Pro
                    165                 170                 175
Ala Pro Gly Glu Gly Pro Pro Gly Thr Val Leu Glu Pro Gln Ser
                    180                 185                 190
Ala Pro Glu Ser Ser Cys Pro Cys Arg Gly Ser Val Lys Asn Gln Pro
                    195                 200                 205
Ser Glu Glu Leu Pro Asp Met Thr Thr Phe Pro Pro Arg Leu Leu Ala
            210                 215                 220
Glu Gln Leu Thr Leu Met Asp Ala Glu Leu Phe Lys Lys Val Val Leu
225                 230                 235                 240
His Glu Cys Leu Gly Cys Ile Trp Gly Gln Gly His Leu Lys Gly Asn
                    245                 250                 255
Glu His Met Ala Pro Thr Val Arg Ala Thr Ile Ala His Phe Asn Arg
                260                 265                 270
Leu Thr Asn Cys Ile Thr Thr Ser Cys Leu Gly Asp His Ser Met Arg
                275                 280                 285
Ala Arg Asp Arg Ala Arg Val Val Glu His Trp Ile Lys Val Ala Arg
            290                 295                 300
Glu Cys Leu Ser Leu Asn Asn Phe Ser Ser Val His Val Ile Val Ser
305                 310                 315                 320
Ala Leu Cys Ser Asn Pro Ile Gly Gln Leu His Lys Thr Trp Ala Gly
                    325                 330                 335
Val Ser Ser Lys Ser Met Lys Glu Leu Lys Glu Leu Cys Lys Lys Asp
                340                 345                 350
Thr Ala Val Lys Arg Asp Leu Leu Ile Lys Ala Gly Ser Phe Lys Val
            355                 360                 365
Ala Thr Gln Glu Arg Asn Pro Gln Arg Val Gln Met Arg Leu Arg Arg
            370                 375                 380
Gln Lys Lys Gly Val Val Pro Phe Leu Gly Asp Phe Leu Thr Glu Leu
385                 390                 395                 400
Gln Arg Leu Asp Ser Ala Ile Pro Asp Asp Leu Asp Gly Asn Thr Asn
                    405                 410                 415
Lys Arg Ser Lys Glu Val Arg Val Leu Gln Glu Met Gln Leu Leu Gln
                420                 425                 430
Val Ala Ala Met Asn Tyr Arg Leu Arg Pro Leu Glu Lys Phe Val Thr
            435                 440                 445
Tyr Phe Thr Arg Met Glu Gln Leu Ser Asp Lys Glu Ser Tyr Lys Leu
        450                 455                 460
Ser Cys Gln Leu Glu Pro Glu Asn Pro
465                 470

<210> SEQ ID NO 3
```

-continued

<211> LENGTH: 32
<212> TYPE: DNA
<213> ORGANISM: Artificial
<220> FEATURE:
<223> OTHER INFORMATION: Synthetic

<400> SEQUENCE: 3
atgacggtga gaacaacggc aacagctaca gg                                32

<210> SEQ ID NO 4
<211> LENGTH: 26
<212> TYPE: DNA
<213> ORGANISM: Artificial
<220> FEATURE:
<223> OTHER INFORMATION: Synthetic

<400> SEQUENCE: 4
cgggttttcg ggctccagct ggcagg                                       26

<210> SEQ ID NO 5
<211> LENGTH: 128
<212> TYPE: DNA
<213> ORGANISM: Homo sapiens

<400> SEQUENCE: 5
tgagggtgct cgtgcctggt tcttcctcag agggatgacg gtgagaacaa cggcaacagc     60
tacaggaaac tgagccctca gaggccctgt gaggtagctg tggtttgcat cactctttac   120
agaagagg                                                           128

<210> SEQ ID NO 6
<211> LENGTH: 70
<212> TYPE: DNA
<213> ORGANISM: Homo sapiens

<400> SEQUENCE: 6
aaacagtctc agggaggccc ggctgcaaga ctgggtgaca cacacaggga gtgtggatct     60
gggccagtgg                                                         70

<210> SEQ ID NO 7
<211> LENGTH: 117
<212> TYPE: DNA
<213> ORGANISM: Homo sapiens
<220> FEATURE:
<221> NAME/KEY: CDS
<222> LOCATION: (2)..(115)

<400> SEQUENCE: 7 t atg agc acg gtg cca ggt ggc tcc cgc cac tcc ctg ggg atc caa gtg     49
  Met Ser Thr Val Pro Gly Gly Ser Arg His Ser Leu Gly Ile Gln Val
  1               5                   10                  15 cgg ggt ggc tgg ggt gta act ggg gga gag gag gag agc ctc act gtc      97
Arg Gly Gly Trp Gly Val Thr Gly Gly Glu Glu Glu Ser Leu Thr Val
            20                  25                  30 cct gtc gct gac acc tgg ca                                          117
Pro Val Ala Asp Thr Trp
        35

<210> SEQ ID NO 8
<211> LENGTH: 38
<212> TYPE: PRT
<213> ORGANISM: Homo sapiens

<400> SEQUENCE: 8

```
Met Ser Thr Val Pro Gly Gly Ser Arg His Ser Leu Gly Ile Gln Val
1               5                   10                  15

Arg Gly Gly Trp Gly Val Thr Gly Gly Glu Glu Ser Leu Thr Val
                20                  25                  30

Pro Val Ala Asp Thr Trp
            35

<210> SEQ ID NO 9
<211> LENGTH: 840
<212> TYPE: DNA
<213> ORGANISM: Homo sapiens
<220> FEATURE:
<221> NAME/KEY: CDS
<222> LOCATION: (251)..(532)

<400> SEQUENCE: 9
```

| | |
|---|---:|
| tgagggtgct cgtgcctggt tcttcctcag agggatgacg gtgagaacaa cggcaacagc | 60 |
| tacaggaaac tgagccctca gaggccctgt gaggtagctg tggtttgcat cactctttac | 120 |
| agaagaggaa acagtctcag ggaggcccgg ctgcaagact gggtgacaca cacagggagt | 180 |
| gtggatctgg gccagtgggg cggggagctt aaggtggcc acccaggaga ggaaccccca | 240 |

```
gagagtccag atg agg ctg cgg agg cag aag aag ggt gtg gtc ccc ttc        289
            Met Arg Leu Arg Arg Gln Lys Lys Gly Val Val Pro Phe
              1               5                   10 ctg ggg gat ttt ctg act gag tta cag agg ctg gat tcg gcc atc ccg        337
Leu Gly Asp Phe Leu Thr Glu Leu Gln Arg Leu Asp Ser Ala Ile Pro
         15                  20                  25 gac gac ctg gat ggc aac acc aac aag agg agc aag gag gtc cga gtt        385
Asp Asp Leu Asp Gly Asn Thr Asn Lys Arg Ser Lys Glu Val Arg Val
 30                  35                  40                  45 ctg cag gaa atg cag ctg ctc caa gtg gct gcc atg aat tac agg ctt        433
Leu Gln Glu Met Gln Leu Leu Gln Val Ala Ala Met Asn Tyr Arg Leu
                 50                  55                  60 cgg cct ctt gag aaa ttt gtc acc tat ttc aca aga atg gag cag ctc        481
Arg Pro Leu Glu Lys Phe Val Thr Tyr Phe Thr Arg Met Glu Gln Leu
             65                  70                  75 agt gac aaa gag agc tac aag ctg tcc tgc cag ctg gag ccc gaa aac        529
Ser Asp Lys Glu Ser Tyr Lys Leu Ser Cys Gln Leu Glu Pro Glu Asn
         80                  85                  90
```

| | |
|---|---:|
| ccg taggctggca acatcctgca gtggctggga acccaccggg atgctggcca | 582 |
| Pro | |
| gaacaccggc tctgcaccat ccctcaccca gaccgtagac accagggaac acatctagg | 642 |
| aggctggcag ctcagctgca tcttgccctg gatcctcatc accaactgct cctgctggcc | 702 |
| aggatcaggc catgggactt tgtgagtca ggcgggagac cattttatgt ttattttctt | 762 |
| tagtgtataa gtaagggttt tttcttaact ttcgttaaaa taaaatttta aaaaactatt | 822 |
| caaaataaaa aaaaaaaa | 840 |

```
<210> SEQ ID NO 10
<211> LENGTH: 94
<212> TYPE: PRT
<213> ORGANISM: Homo sapiens

<400> SEQUENCE: 10

Met Arg Leu Arg Arg Gln Lys Lys Gly Val Val Pro Phe Leu Gly Asp
1               5                   10                  15

Phe Leu Thr Glu Leu Gln Arg Leu Asp Ser Ala Ile Pro Asp Asp Leu
                20                  25                  30
```

```
Asp Gly Asn Thr Asn Lys Arg Ser Lys Glu Val Arg Val Leu Gln Glu
        35                  40                  45

Met Gln Leu Leu Gln Val Ala Ala Met Asn Tyr Arg Leu Arg Pro Leu
 50                  55                  60

Glu Lys Phe Val Thr Tyr Phe Thr Arg Met Glu Gln Leu Ser Asp Lys
 65                  70                  75                  80

Glu Ser Tyr Lys Leu Ser Cys Gln Leu Glu Pro Glu Asn Pro
                 85                  90

<210> SEQ ID NO 11
<211> LENGTH: 966
<212> TYPE: DNA
<213> ORGANISM: Homo sapiens
<220> FEATURE:
<221> NAME/KEY: CDS
<222> LOCATION: (251)..(658)

<400> SEQUENCE: 11
tgagggtgct cgtgcctggt tcttcctcag agggatgacg gtgagaacaa cggcaacagc      60
tacaggaaac tgagccctca gaggcccgtg gaggtagctg tggtttgcat cactctttac     120
agaagaggaa acagtctcag gaggcccgg ctgcaagact gggtgacaca cacagggagt     180
gtggatctgg gccagtgggg cggggagctt aaggtggcc acccaggaga ggaaccccca     240
gagagtccag atg agg ctg cgg agg cag aag aag ggt gtg gtc ccc ttc        289
            Met Arg Leu Arg Arg Gln Lys Lys Gly Val Val Pro Phe
             1               5                  10 ctg ggg gat ttt ctg act gag tta cag agg ctg gat tcg gcc atc ccg       337
Leu Gly Asp Phe Leu Thr Glu Leu Gln Arg Leu Asp Ser Ala Ile Pro
 15                  20                  25 gac gac ctg gat ggc aac acc aac aag agg agc aag gag gtc cga gtt       385
Asp Asp Leu Asp Gly Asn Thr Asn Lys Arg Ser Lys Glu Val Arg Val
 30                  35                  40                  45 ctg cag gaa atg cag ctg ctc caa gtg gct gcc atg aat tac agg ctt       433
Leu Gln Glu Met Gln Leu Leu Gln Val Ala Ala Met Asn Tyr Arg Leu
                 50                  55                  60 cgg cct ctt gag aaa ttt gtc acc tat ttc aca aga atg gag cag ctc       481
Arg Pro Leu Glu Lys Phe Val Thr Tyr Phe Thr Arg Met Glu Gln Leu
             65                  70                  75 agt gac aaa gag agg ctg cac tgc agt gtc acc atc tct gtt cac tgc       529
Ser Asp Lys Glu Arg Leu His Cys Ser Val Thr Ile Ser Val His Cys
         80                  85                  90 aac gtc tgc ctt ctg ggc tca agt cct tcc tca gcc tcc caa gca gct       577
Asn Val Cys Leu Leu Gly Ser Ser Pro Ser Ser Ala Ser Gln Ala Ala
     95                  100                 105 ggg act acc gct gta cac cac cat gtc cgg ttg ttc tgc tgt tgc tac       625
Gly Thr Thr Ala Val His His His Val Arg Leu Phe Cys Cys Cys Tyr
110                 115                 120                 125 aag ctg tcc tgc cag ctg gag ccc gaa aac ccg taggctgca acatcctgca      678
Lys Leu Ser Cys Gln Leu Glu Pro Glu Asn Pro
                 130                 135 gtggctggga acccaccggg atgctggcca gaacaccggc tctgcaccat ccctcaccca     738
gaccgtagac accagggaac cacatctagg aggctggcag ctcagctgca tcttgccctg     798
gatcctcatc accaactgct cctgctggcc aggatcaggc catgggactt tgtgagtca     858 ggcgggagac catttatgt ttattttctt tagtgtataa gtaagggttt tttcttaact      918
ttcgttaaaa taaattta aaaaactatt caaaataaaa aaaaaaaa                    966

<210> SEQ ID NO 12
```

<211> LENGTH: 136
<212> TYPE: PRT
<213> ORGANISM: Homo sapiens

<400> SEQUENCE: 12

Met Arg Leu Arg Arg Gln Lys Lys Gly Val Val Pro Phe Leu Gly Asp
1               5                   10                  15

Phe Leu Thr Glu Leu Gln Arg Leu Asp Ser Ala Ile Pro Asp Asp Leu
            20                  25                  30

Asp Gly Asn Thr Asn Lys Arg Ser Lys Glu Val Arg Val Leu Gln Glu
        35                  40                  45

Met Gln Leu Leu Gln Val Ala Ala Met Asn Tyr Arg Leu Arg Pro Leu
    50                  55                  60

Glu Lys Phe Val Thr Tyr Phe Thr Arg Met Glu Gln Leu Ser Asp Lys
65                  70                  75                  80

Glu Arg Leu His Cys Ser Val Thr Ile Ser Val His Cys Asn Val Cys
                85                  90                  95

Leu Leu Gly Ser Ser Pro Ser Ser Ala Ser Gln Ala Ala Gly Thr Thr
            100                 105                 110

Ala Val His His His Val Arg Leu Phe Cys Cys Cys Tyr Lys Leu Ser
        115                 120                 125

Cys Gln Leu Glu Pro Glu Asn Pro
    130                 135

<210> SEQ ID NO 13
<211> LENGTH: 964
<212> TYPE: DNA
<213> ORGANISM: Homo sapiens
<220> FEATURE:
<221> NAME/KEY: CDS
<222> LOCATION: (200)..(649)

<400> SEQUENCE: 13
tgagggtgct cgtgcctggt tcttcctcag agggatgacg gtgagaacaa cggcaacagc      60
tacaggaaac tgagccctca gaggccctgt gaggtagctg tggtttgcat cactcttttac    120 agaagaggaa acagtctcag ggaggcccgg ctgcaagact gggtgacaca cacagggagt     180
gtggatctgg gccagtggt atg agc acg gtg cca ggt ggc tcc cgc cac tcc      232
                     Met Ser Thr Val Pro Gly Gly Ser Arg His Ser
                     1               5                   10 ctg ggg atc caa gtg cgg ggt ggc tgg ggt gta act ggg gga gag gag       280
Leu Gly Ile Gln Val Arg Gly Gly Trp Gly Val Thr Gly Gly Glu Glu
            15                  20                  25 gag agc ctc act gtc cct gtc gct gac acc tgg cag gcg ggg agc ttt       328
Glu Ser Leu Thr Val Pro Val Ala Asp Thr Trp Gln Ala Gly Ser Phe
        30                  35                  40 aag gtg gcc acc cag gag agg aac ccc cag aga gtc cag atg agg ctg       376
Lys Val Ala Thr Gln Glu Arg Asn Pro Gln Arg Val Gln Met Arg Leu
    45                  50                  55 cgg agg cag aag aag ggt gtg gtc ccc ttc ctg ggg gat ttt ctg act       424
Arg Arg Gln Lys Lys Gly Val Val Pro Phe Leu Gly Asp Phe Leu Thr
60                  65                  70                  75 gag tta cag agg ctg gat tcg gcc atc ccg gac gac ctg gat ggc aac       472
Glu Leu Gln Arg Leu Asp Ser Ala Ile Pro Asp Asp Leu Asp Gly Asn
                80                  85                  90 acc aac aag agg agc aag gag gtc cga gtt ctg cag gaa atg cag ctg       520
Thr Asn Lys Arg Ser Lys Glu Val Arg Val Leu Gln Glu Met Gln Leu
            95                  100                 105 ctc caa gtg gct gcc atg aat tac agg ctt cgg cct ctt gag aaa ttt       568

```
Leu Gln Val Ala Ala Met Asn Tyr Arg Leu Arg Pro Leu Glu Lys Phe
        110                 115                 120 gtc acc tat ttc aca aga atg gag cag ctc agt gac aaa gag agc tac    616
Val Thr Tyr Phe Thr Arg Met Glu Gln Leu Ser Asp Lys Glu Ser Tyr
    125                 130                 135 aag ctg tcc tgc cag ctg gag ccc gaa aac ccg taggctggca acatcctgca  669
Lys Leu Ser Cys Gln Leu Glu Pro Glu Asn Pro
140                 145                 150 gtggctggga acccacgggg atgctggcca gaacaccggc tctgcaccat ccctcaccca  729
gaccgtagac accagggaac cacatctagg aggctggcag ctcagctgca tcttgccctg  789
gatcctcatc accaactgct cctctggcca ggatcaggcc atgggacttt tgtgagtcag  849
gcgggagacc attttatgtt tattttcttt agtgtataag taagggtttt ttcttaactt  909
tcgttaaaat aaaattttaa aaactattc aaaataaaaa aaaaaaaaaa aaaaa        964

<210> SEQ ID NO 14
<211> LENGTH: 150
<212> TYPE: PRT
<213> ORGANISM: Homo sapiens

<400> SEQUENCE: 14

Met Ser Thr Val Pro Gly Gly Ser Arg His Ser Leu Gly Ile Gln Val
1               5                   10                  15

Arg Gly Gly Trp Gly Val Thr Gly Gly Glu Glu Ser Leu Thr Val
                20                  25                  30

Pro Val Ala Asp Thr Trp Gln Ala Gly Ser Phe Lys Val Ala Thr Gln
            35                  40                  45

Glu Arg Asn Pro Gln Arg Val Gln Met Arg Leu Arg Arg Gln Lys Lys
        50                  55                  60

Gly Val Val Pro Phe Leu Gly Asp Phe Leu Thr Glu Leu Gln Arg Leu
65                  70                  75                  80

Asp Ser Ala Ile Pro Asp Asp Leu Asp Gly Asn Thr Asn Lys Arg Ser
                85                  90                  95

Lys Glu Val Arg Val Leu Gln Glu Met Gln Leu Leu Gln Val Ala Ala
            100                 105                 110

Met Asn Tyr Arg Leu Arg Pro Leu Glu Lys Phe Val Thr Tyr Phe Thr
        115                 120                 125

Arg Met Glu Gln Leu Ser Asp Lys Glu Ser Tyr Lys Leu Ser Cys Gln
    130                 135                 140

Leu Glu Pro Glu Asn Pro
145                 150

<210> SEQ ID NO 15
<211> LENGTH: 1048
<212> TYPE: DNA
<213> ORGANISM: Homo sapiens
<220> FEATURE:
<221> NAME/KEY: CDS
<222> LOCATION: (200)..(970)

<400> SEQUENCE: 15
tgagggtgct cgtgcctggt tcttcctcag agggatgacg gtgagaacaa cggcaacagc    60
tacaggaaac tgagccctca gaggcccgt gaggtagctg tggtttgcat cactcttttac   120 agaagaggaa acagtctcag ggaggcccgg ctgcaagact gggtgacaca cacagggagt   180
gtggatctgg gccagtggt atg agc acg gtg cca ggt ggc tcc cgc cac tcc    232
                     Met Ser Thr Val Pro Gly Gly Ser Arg His Ser
                     1               5                   10
```

-continued

| | |
|---|---|
| ctg ggg atc caa gtg cgg ggt ggc tgg ggt gta act ggg gga gag gag<br>Leu Gly Ile Gln Val Arg Gly Gly Trp Gly Val Thr Gly Gly Glu Glu<br>              15                    20                  25 | 280 |
| gag agc ctc act gtc cct gtc gct gac acc tgg cag gcg ggg agc ttt<br>Glu Ser Leu Thr Val Pro Val Ala Asp Thr Trp Gln Ala Gly Ser Phe<br>          30                  35                  40 | 328 |
| aag gtg gcc acc cag gag agg aac ccc cag aga gtc cag atg agg ctg<br>Lys Val Ala Thr Gln Glu Arg Asn Pro Gln Arg Val Gln Met Arg Leu<br>45                    50                  55 | 376 |
| cgg agg cag aag aag ggt gtg gtc ccc ttc ctg ggg gat ttt ctg act<br>Arg Arg Gln Lys Lys Gly Val Val Pro Phe Leu Gly Asp Phe Leu Thr<br>60                    65                  70                  75 | 424 |
| gag tta cag agg ctg gat tcg gcc atc ccg gac gac ctg gat ggc aac<br>Glu Leu Gln Arg Leu Asp Ser Ala Ile Pro Asp Asp Leu Asp Gly Asn<br>                80                  85                  90 | 472 |
| acc aac aag agg agc aag gag gtc cga gtt ctg cag gaa atg cag ctg<br>Thr Asn Lys Arg Ser Lys Glu Val Arg Val Leu Gln Glu Met Gln Leu<br>          95                  100               105 | 520 |
| ctc caa gtg gct gcc atg aat tac agg ctt cgg cct ctt gag aaa ttt<br>Leu Gln Val Ala Ala Met Asn Tyr Arg Leu Arg Pro Leu Glu Lys Phe<br>               110               115               120 | 568 |
| gtc acc tat ttc aca aga atg gag cag ctc agt gac aaa gag agg ggg<br>Val Thr Tyr Phe Thr Arg Met Glu Gln Leu Ser Asp Lys Glu Arg Gly<br>125                 130               135 | 616 |
| ttt cac gat gat gtc cag gat cgt ctc aaa ctc ctg gcc tca agc aat<br>Phe His Asp Asp Val Gln Asp Arg Leu Lys Leu Leu Ala Ser Ser Asn<br>140                 145               150               155 | 664 |
| cca ccc acc tca gcc tcc caa agt act gac gtt aca ggt cta caa gct<br>Pro Pro Thr Ser Ala Ser Gln Ser Thr Asp Val Thr Gly Leu Gln Ala<br>               160               165               170 | 712 |
| gtc ctg cca gct gga gcc cga aaa ccc gta ggc tgg caa cat cct gca<br>Val Leu Pro Ala Gly Ala Arg Lys Pro Val Gly Trp Gln His Pro Ala<br>175                 180               185 | 760 |
| gtg gct ggg aac cca ccg gga tgc tgg cca gaa cac cgg ctc tgc acc<br>Val Ala Gly Asn Pro Pro Gly Cys Trp Pro Glu His Arg Leu Cys Thr<br>190                 195               200 | 808 |
| atc cct cac cca gac cgt aga cac cag gga acc aca tct agg agg ctg<br>Ile Pro His Pro Asp Arg Arg His Gln Gly Thr Thr Ser Arg Arg Leu<br>205                 210               215 | 856 |
| gca gct cag ctg cat ctt gcc ctg gat cct cat cac caa ctg ctc ctg<br>Ala Ala Gln Leu His Leu Ala Leu Asp Pro His His Gln Leu Leu Leu<br>220                 225               230               235 | 904 |
| ctg gcc agg atc agg cca tgg gac ttt tgt gag tca ggc ggg aga cca<br>Leu Ala Arg Ile Arg Pro Trp Asp Phe Cys Glu Ser Gly Gly Arg Pro<br>               240               245               250 | 952 |
| ttt tat gtt tat ttt ctt tagtgtataa gtaagggttt tttcttaact<br>Phe Tyr Val Tyr Phe Leu<br>255 | 1000 |
| ttcgttaaaa taaattttta aaaactatt caaataaaa aaaaaaa | 1048 |

<210> SEQ ID NO 16
<211> LENGTH: 257
<212> TYPE: PRT
<213> ORGANISM: Homo sapiens

<400> SEQUENCE: 16

Met Ser Thr Val Pro Gly Gly Ser Arg His Ser Leu Gly Ile Gln Val
1                   5                   10                 15

Arg Gly Gly Trp Gly Val Thr Gly Gly Glu Glu Glu Ser Leu Thr Val

-continued

```
                    20                  25                  30
Pro Val Ala Asp Thr Trp Gln Ala Gly Ser Phe Lys Val Ala Thr Gln
                35                  40                  45
Glu Arg Asn Pro Gln Arg Val Gln Met Arg Leu Arg Arg Gln Lys Lys
            50                  55                  60
Gly Val Val Pro Phe Leu Gly Asp Phe Leu Thr Glu Leu Gln Arg Leu
65                  70                  75                  80
Asp Ser Ala Ile Pro Asp Asp Leu Asp Gly Asn Thr Asn Lys Arg Ser
                85                  90                  95
Lys Glu Val Arg Val Leu Gln Glu Met Gln Leu Leu Gln Val Ala Ala
            100                 105                 110
Met Asn Tyr Arg Leu Arg Pro Leu Glu Lys Phe Val Thr Tyr Phe Thr
        115                 120                 125
Arg Met Glu Gln Leu Ser Asp Lys Glu Arg Gly Phe His Asp Asp Val
    130                 135                 140
Gln Asp Arg Leu Lys Leu Leu Ala Ser Ser Asn Pro Pro Thr Ser Ala
145                 150                 155                 160
Ser Gln Ser Thr Asp Val Thr Gly Leu Gln Ala Val Leu Pro Ala Gly
                165                 170                 175
Ala Arg Lys Pro Val Gly Trp Gln His Pro Ala Val Ala Gly Asn Pro
            180                 185                 190
Pro Gly Cys Trp Pro Glu His Arg Leu Cys Thr Ile Pro His Pro Asp
        195                 200                 205
Arg Arg His Gln Gly Thr Thr Ser Arg Arg Leu Ala Ala Gln Leu His
    210                 215                 220
Leu Ala Leu Asp Pro His His Gln Leu Leu Leu Ala Arg Ile Arg
225                 230                 235                 240
Pro Trp Asp Phe Cys Glu Ser Gly Gly Arg Pro Phe Tyr Val Tyr Phe
                245                 250                 255
Leu
```

<210> SEQ ID NO 17
<211> LENGTH: 1240
<212> TYPE: DNA
<213> ORGANISM: Homo sapiens
<220> FEATURE:
<221> NAME/KEY: CDS
<222> LOCATION: (200)..(622)

<400> SEQUENCE: 17

```
tgagggtgct cgtgcctggt tcttcctcag agggatgacg gtgagaacaa cggcaacagc      60
tacaggaaac tgagccctca gaggccctgt gaggtagctg tggtttgcat cactctttac     120
agaagaggaa acagtctcag gaggcccggg ctgcaagact gggtgacaca cacagggagt     180
gtggatctgg gccagtggt atg agc acg gtg cca ggt ggc tcc cgc cac tcc     232
                     Met Ser Thr Val Pro Gly Gly Ser Arg His Ser
                       1               5                   10 ctg ggg atc caa gtg cgg ggt ggc tgg ggt gta act ggg gga gag gag     280
Leu Gly Ile Gln Val Arg Gly Gly Trp Gly Val Thr Gly Gly Glu Glu
            15                  20                  25 gag agc ctc act gtc cct gtc gct gac acc tgg cag gcg ggg agc ttt     328
Glu Ser Leu Thr Val Pro Val Ala Asp Thr Trp Gln Ala Gly Ser Phe
        30                  35                  40 aag gtg gcc acc cag gag agg aac ccc cag aga gtc cag atg agg ctg     376
Lys Val Ala Thr Gln Glu Arg Asn Pro Gln Arg Val Gln Met Arg Leu
    45                  50                  55
```

```
cgg agg cag aag aag ggt gtg gtc ccc ttc ctg ggg gat ttt ctg act    424
Arg Arg Gln Lys Lys Gly Val Val Pro Phe Leu Gly Asp Phe Leu Thr
 60              65                  70                  75 gag tta cag agg ctg gat tcg gcc atc ccg gac gac ctg gat ggc aac    472
Glu Leu Gln Arg Leu Asp Ser Ala Ile Pro Asp Asp Leu Asp Gly Asn
             80                  85                  90 acc aac aag agg agc aag gag gtc cga gtt ctg cag gaa atg cag ctg    520
Thr Asn Lys Arg Ser Lys Glu Val Arg Val Leu Gln Glu Met Gln Leu
         95                 100                 105 ctc caa gtg gct gcc atg aat tac agg ctt cgg cct ctt gag aaa ttt    568
Leu Gln Val Ala Ala Met Asn Tyr Arg Leu Arg Pro Leu Glu Lys Phe
                110                 115                 120 gtc acc tat ttc aca aga atg gag cag ctc agt gac aaa gag ggg gtt    616
Val Thr Tyr Phe Thr Arg Met Glu Gln Leu Ser Asp Lys Glu Gly Val
            125                 130                 135 tca cga tgatgtccag gatcgtctca aactcctggc ctcaagcaat ccacccacct     672
Ser Arg
140 cagcctccca agtactgac gttacaggtg tgagccaccc cacctggcct agagaggctc    732 tcccgtggcc agctgcagag agcctatggc catgcctcca cggccagcat caagccctgt    792 tgcatgggga ccactgggga cccaggattc agctgggca ggcactgaca ggggacctga     852 tgtgtgctc atggtggcct cacagctgct tctctgtcct gcctacaagc tgtcctgcca     912 gctggagccc gaaaacccgt aggctggcaa catcctgcag tggctgggaa cccaccggga    972 tgctggccag acaccggct ctgcaccatc cctcacccag accgtagaca ccaggggaac    1032 cacatctagg aggctggcag ctcagctgca tcttgccctg gatcctcatc accaactgct   1092 cctgctggcc aggatcaggc catgggactt tgtgagtca ggcgggagac cattttatgt    1152 ttattttctt tagtgtataa gtaagggttt tttcttaact ttcgttaaaa taaaatttta   1212 aaaaactatt caaataaaaa aaaaaaaa                                      1240

<210> SEQ ID NO 18
<211> LENGTH: 141
<212> TYPE: PRT
<213> ORGANISM: Homo sapiens

<400> SEQUENCE: 18

Met Ser Thr Val Pro Gly Gly Ser Arg His Ser Leu Gly Ile Gln Val
 1               5                  10                  15

Arg Gly Gly Trp Gly Val Thr Gly Gly Glu Glu Ser Leu Thr Val
            20                  25                  30

Pro Val Ala Asp Thr Trp Gln Ala Gly Ser Phe Lys Val Ala Thr Gln
            35                  40                  45

Glu Arg Asn Pro Gln Arg Val Gln Met Arg Leu Arg Gln Lys Lys
 50                  55                  60

Gly Val Val Pro Phe Leu Gly Asp Phe Leu Thr Glu Leu Gln Arg Leu
 65                  70                  75                  80

Asp Ser Ala Ile Pro Asp Asp Leu Asp Gly Asn Thr Asn Lys Arg Ser
                 85                  90                  95

Lys Glu Val Arg Val Leu Gln Glu Met Gln Leu Leu Gln Val Ala Ala
            100                 105                 110

Met Asn Tyr Arg Leu Arg Pro Leu Glu Lys Phe Val Thr Tyr Phe Thr
            115                 120                 125

Arg Met Glu Gln Leu Ser Asp Lys Glu Gly Val Ser Arg
        130                 135                 140
```

<210> SEQ ID NO 19
<211> LENGTH: 529
<212> TYPE: DNA
<213> ORGANISM: Homo sapiens
<220> FEATURE:
<221> NAME/KEY: CDS
<222> LOCATION: (14)..(463)

<400> SEQUENCE: 19

```
ctgggccagt ggt atg agc acg gtg cca ggt ggc tcc cgc cac tcc ctg        49
            Met Ser Thr Val Pro Gly Gly Ser Arg His Ser Leu
            1               5                   10 ggg atc caa gtg cgg ggt ggc tgg ggt gta act ggg gga gag gag gag       97
Gly Ile Gln Val Arg Gly Gly Trp Gly Val Thr Gly Gly Glu Glu Glu
        15                  20                  25 agc ctc act gtc cct gtc gct gac acc tgg cag gcg ggg agc ttt aag      145
Ser Leu Thr Val Pro Val Ala Asp Thr Trp Gln Ala Gly Ser Phe Lys
    30                  35                  40 gtg gcc acc cag gag agg aac ccc cag aga gtc cag atg agg ctg cgg      193
Val Ala Thr Gln Glu Arg Asn Pro Gln Arg Val Gln Met Arg Leu Arg
45                  50                  55                  60 agg cag aag aag ggt gtg gtc ccc ttc ctg ggg gat ttt ctg act gag      241
Arg Gln Lys Lys Gly Val Val Pro Phe Leu Gly Asp Phe Leu Thr Glu
                65                  70                  75 tta cag agg ctg gat tcg gcc atc ccg gac gac ctg gat ggc aac acc      289
Leu Gln Arg Leu Asp Ser Ala Ile Pro Asp Asp Leu Asp Gly Asn Thr
        80                  85                  90 aac aag agg agc aag gag gtc cga gtt ctg cag gaa atg cag ctg ctc      337
Asn Lys Arg Ser Lys Glu Val Arg Val Leu Gln Glu Met Gln Leu Leu
    95                 100                 105 caa gtg gct gcc atg aat tac agg ctt cgg cct ctt gag aaa ttt gtc      385
Gln Val Ala Ala Met Asn Tyr Arg Leu Arg Pro Leu Glu Lys Phe Val
110                 115                 120 acc tat ttc aca aga atg gag cag ctc agt gac aaa gag agc tac aag      433
Thr Tyr Phe Thr Arg Met Glu Gln Leu Ser Asp Lys Glu Ser Tyr Lys
125                 130                 135                 140 ctg tcc tgc cag ctg gag ccc gaa aac ccg tagggttttt tcttaacttt       483
Leu Ser Cys Gln Leu Glu Pro Glu Asn Pro
                145                 150 cgttaaaata aaattttaaa aaactattca aaataaaaaa aaaaaa                  529
```

<210> SEQ ID NO 20
<211> LENGTH: 150
<212> TYPE: PRT
<213> ORGANISM: Homo sapiens

<400> SEQUENCE: 20

```
Met Ser Thr Val Pro Gly Gly Ser Arg His Ser Leu Gly Ile Gln Val
1               5                   10                  15

Arg Gly Gly Trp Gly Val Thr Gly Gly Glu Glu Glu Ser Leu Thr Val
            20                  25                  30

Pro Val Ala Asp Thr Trp Gln Ala Gly Ser Phe Lys Val Ala Thr Gln
        35                  40                  45

Glu Arg Asn Pro Gln Arg Val Gln Met Arg Leu Arg Arg Gln Lys Lys
    50                  55                  60

Gly Val Val Pro Phe Leu Gly Asp Phe Leu Thr Glu Leu Gln Arg Leu
65                  70                  75                  80

Asp Ser Ala Ile Pro Asp Asp Leu Asp Gly Asn Thr Asn Lys Arg Ser
                85                  90                  95
```

Lys Glu Val Arg Val Leu Gln Glu Met Gln Leu Leu Gln Val Ala Ala
            100                 105                 110

Met Asn Tyr Arg Leu Arg Pro Leu Glu Lys Phe Val Thr Tyr Phe Thr
        115                 120                 125

Arg Met Glu Gln Leu Ser Asp Lys Glu Ser Tyr Lys Leu Ser Cys Gln
    130                 135                 140

Leu Glu Pro Glu Asn Pro
145                 150

<210> SEQ ID NO 21
<211> LENGTH: 771
<212> TYPE: DNA
<213> ORGANISM: Homo sapiens
<220> FEATURE:
<221> NAME/KEY: CDS
<222> LOCATION: (181)..(462)

<400> SEQUENCE: 21
tgagggtgct cgtgcctggt tcttcctcag agggatgacg gtgagaacaa cggcaacagc      60
tacaggaaac tgagccctca gaggccctgt gaggtagctg tggtttgcat cactctttac     120
agaagagggg cggggagctt taaggtggcc acccaggaga ggaaccccca gagagtccag     180 atg agg ctg cgg agg cag aag aag ggt gtg gtc ccc ttc ctg ggg gat      228
Met Arg Leu Arg Arg Gln Lys Lys Gly Val Val Pro Phe Leu Gly Asp
1               5                   10                  15 ttt ctg act gag tta cag agg ctg gat tcg gcc atc ccg gac gac ctg      276
Phe Leu Thr Glu Leu Gln Arg Leu Asp Ser Ala Ile Pro Asp Asp Leu
                20                  25                  30 gat ggc aac acc aac aag agg agc aag gag gtc cga gtt ctg cag gaa      324
Asp Gly Asn Thr Asn Lys Arg Ser Lys Glu Val Arg Val Leu Gln Glu
            35                  40                  45 atg cag ctg ctc caa gtg gct gcc atg aat tac agg ctt cgg cct ctt      372
Met Gln Leu Leu Gln Val Ala Ala Met Asn Tyr Arg Leu Arg Pro Leu
        50                  55                  60 gag aaa ttt gtc acc tat ttc aca aga atg gag cag ctc agt gac aaa      420
Glu Lys Phe Val Thr Tyr Phe Thr Arg Met Glu Gln Leu Ser Asp Lys
65                  70                  75                  80 gag agc tac aag ctg tcc tgc cag ctg gag ccc gaa aac ccg              462
Glu Ser Tyr Lys Leu Ser Cys Gln Leu Glu Pro Glu Asn Pro
                85                  90 taggctggca acatcctgca gtggctggga acccaccggg atgctggcca gaacaccggc     522
tctgcaccat ccctcaccca gacccgtaga caccagggaa ccacatctag gaggctggca     582
gctcagctgc atcttgccct ggatcctcat caccaactgc tcctgctggc aggatcagg      642 ccatgggact tttgtgagtc aggcgggaga ccatttttatg tttatttct ttagtgtata     702 agtaagggtt ttttcttaac tttcgttaaa ataaatttt aaaaaactat tcaaaataaa      762
aaaaaaaaa                                                            771

<210> SEQ ID NO 22
<211> LENGTH: 94
<212> TYPE: PRT
<213> ORGANISM: Homo sapiens

<400> SEQUENCE: 22

Met Arg Leu Arg Arg Gln Lys Lys Gly Val Val Pro Phe Leu Gly Asp
1               5                   10                  15

Phe Leu Thr Glu Leu Gln Arg Leu Asp Ser Ala Ile Pro Asp Asp Leu
                20                  25                  30

```
Asp Gly Asn Thr Asn Lys Arg Ser Lys Glu Val Arg Val Leu Gln Glu
            35                  40                  45

Met Gln Leu Leu Gln Val Ala Ala Met Asn Tyr Arg Leu Arg Pro Leu
 50                  55                  60

Glu Lys Phe Val Thr Tyr Phe Thr Arg Met Glu Gln Leu Ser Asp Lys
 65                  70                  75                  80

Glu Ser Tyr Lys Leu Ser Cys Gln Leu Glu Pro Glu Asn Pro
                85                  90
```

<210> SEQ ID NO 23
<211> LENGTH: 1044
<212> TYPE: DNA
<213> ORGANISM: Homo sapiens
<220> FEATURE:
<221> NAME/KEY: CDS
<222> LOCATION: (196)..(966)

<400> SEQUENCE: 23

```
gggtgctcgt gcctggttct tcctcagagg gatgacggtg agaacaaggc aacagctaca     60
ggaaactgag ccctcagagg ccctgtgagg tagctgtggt ttgcatcact ctttacagaa    120
gaggaaacag tctcagggag gcccggctgc aagactgggg gacacacaca gggagtgtgg    180
atctgggcca gtggt atg agc acg gtg cca ggt ggc tcc cgc cac tcc ctg     231
                 Met Ser Thr Val Pro Gly Gly Ser Arg His Ser Leu
                  1               5                  10 ggg atc caa gtg cgg ggt ggc tgg ggt gta act ggg gga gag gag gag     279
Gly Ile Gln Val Arg Gly Gly Trp Gly Val Thr Gly Gly Glu Glu Glu
             15                  20                  25 agc ctc act gtc cct gtc gct gac acc tgg cag gcg ggg agc ttt aag     327
Ser Leu Thr Val Pro Val Ala Asp Thr Trp Gln Ala Gly Ser Phe Lys
         30                  35                  40 gtg gcc acc cag gag agg aac ccc cag aga gtc cag atg agg ctg cgg     375
Val Ala Thr Gln Glu Arg Asn Pro Gln Arg Val Gln Met Arg Leu Arg
 45                  50                  55                  60 agg cag aag aag ggt gtg gtc ccc ttc ctg ggg gat ttt ctg act gag     423
Arg Gln Lys Lys Gly Val Val Pro Phe Leu Gly Asp Phe Leu Thr Glu
                 65                  70                  75 tta cag agg ctg gat tcg gcc atc ccg gac gac ctg gat ggc aac acc     471
Leu Gln Arg Leu Asp Ser Ala Ile Pro Asp Asp Leu Asp Gly Asn Thr
             80                  85                  90 aac aag agg agc aag gag gtc cga gtt ctg cag gaa atg cag ctg ctc     519
Asn Lys Arg Ser Lys Glu Val Arg Val Leu Gln Glu Met Gln Leu Leu
         95                 100                 105 caa gtg gct gcc atg aat tac agg ctt cgg cct ctt gag aaa ttt gtc     567
Gln Val Ala Ala Met Asn Tyr Arg Leu Arg Pro Leu Glu Lys Phe Val
110                 115                 120 acc tat ttc aca aga atg gag cag ctc agt gac aaa gag aga tgg ggt     615
Thr Tyr Phe Thr Arg Met Glu Gln Leu Ser Asp Lys Glu Arg Trp Gly
125                 130                 135                 140 ttc acg atg atg tcc agg atc gtc tca aac tcc tgg cct caa gca atc     663
Phe Thr Met Met Ser Arg Ile Val Ser Asn Ser Trp Pro Gln Ala Ile
                145                 150                 155 cac cca cct cag cct ccc aaa gta ctg acg tta cag cta caa gct gtc     711
His Pro Pro Gln Pro Pro Lys Val Leu Thr Leu Gln Leu Gln Ala Val
            160                 165                 170 ctg cca gct gga gcc cga aaa ccc gta ggc tgg caa cat cct gca gtg     759
Leu Pro Ala Gly Ala Arg Lys Pro Val Gly Trp Gln His Pro Ala Val
        175                 180                 185 gct ggg aac cca ccg gga tgc tgg cca gaa cac cgg ctc tgc acc atc     807
Ala Gly Asn Pro Pro Gly Cys Trp Pro Glu His Arg Leu Cys Thr Ile
```

|     |     |     |     |     |     |     |     |     |     |     |     |     |     |     |     |      |
|---|---|---|---|---|---|---|---|---|---|---|---|---|---|---|---|---|
|     |     |     | 190 |     |     |     | 195 |     |     |     | 200 |     |     |     |     |      |
| cct | cac | cca | gac | cgt | aga | cac | cag | gga | acc | aca | tct | agg | agg | ctg | gca | 855  |
| Pro | His | Pro | Asp | Arg | Arg | His | Gln | Gly | Thr | Thr | Ser | Arg | Arg | Leu | Ala |      |
| 205 |     |     |     |     | 210 |     |     |     |     | 215 |     |     |     |     | 220 |      |
| gct | cag | ctg | cat | ctt | gcc | ctg | gat | cct | cat | cac | caa | ctg | ctc | ctg | ctg | 903  |
| Ala | Gln | Leu | His | Leu | Ala | Leu | Asp | Pro | His | His | Gln | Leu | Leu | Leu | Leu |      |
|     |     |     |     | 225 |     |     |     |     | 230 |     |     |     |     | 235 |     |      |
| gcc | agg | atc | agg | cca | tgg | gac | ttt | tgt | gag | tca | ggc | ggg | aga | cca | ttt | 951  |
| Ala | Arg | Ile | Arg | Pro | Trp | Asp | Phe | Cys | Glu | Ser | Gly | Gly | Arg | Pro | Phe |      |
|     |     |     | 240 |     |     |     |     | 245 |     |     |     |     | 250 |     |     |      |
| tat | gtt | tat | ttt | ctt | tagtgtataa | | gtaagggttt | | | tttcttaact | | | ttcgttaaaa | | | 1006 |
| Tyr | Val | Tyr | Phe | Leu | | | | | | | | | | | | |
|     |     |     | 255 |     |     |     |     |     |     |     |     |     |     |     |     |      | taaaatttta aaaaactatt caaaataaaa aaaaaaaa                                 1044

<210> SEQ ID NO 24
<211> LENGTH: 257
<212> TYPE: PRT
<213> ORGANISM: Homo sapiens

<400> SEQUENCE: 24

Met Ser Thr Val Pro Gly Gly Ser Arg His Ser Leu Gly Ile Gln Val
1               5                   10                  15

Arg Gly Gly Trp Gly Val Thr Gly Gly Glu Glu Ser Leu Thr Val
            20                  25                  30

Pro Val Ala Asp Thr Trp Gln Ala Gly Ser Phe Lys Val Ala Thr Gln
        35                  40                  45

Glu Arg Asn Pro Gln Arg Val Gln Met Arg Leu Arg Arg Gln Lys Lys
    50                  55                  60

Gly Val Val Pro Phe Leu Gly Asp Phe Leu Thr Glu Leu Gln Arg Leu
65                  70                  75                  80

Asp Ser Ala Ile Pro Asp Asp Leu Asp Gly Asn Thr Asn Lys Arg Ser
                85                  90                  95

Lys Glu Val Arg Val Leu Gln Glu Met Gln Leu Leu Gln Val Ala Ala
            100                 105                 110

Met Asn Tyr Arg Leu Arg Pro Leu Glu Lys Phe Val Thr Tyr Phe Thr
        115                 120                 125

Arg Met Glu Gln Leu Ser Asp Lys Glu Arg Trp Gly Phe Thr Met Met
    130                 135                 140

Ser Arg Ile Val Ser Asn Ser Trp Pro Gln Ala Ile His Pro Pro Gln
145                 150                 155                 160

Pro Pro Lys Val Leu Thr Leu Gln Leu Gln Ala Val Leu Pro Ala Gly
                165                 170                 175

Ala Arg Lys Pro Val Gly Trp Gln His Pro Ala Val Ala Gly Asn Pro
            180                 185                 190

Pro Gly Cys Trp Pro Glu His Arg Leu Cys Thr Ile Pro His Pro Asp
        195                 200                 205

Arg Arg His Gln Gly Thr Thr Ser Arg Arg Leu Ala Ala Gln Leu His
    210                 215                 220

Leu Ala Leu Asp Pro His His Gln Leu Leu Leu Ala Arg Ile Arg
225                 230                 235                 240

Pro Trp Asp Phe Cys Glu Ser Gly Gly Arg Pro Phe Tyr Val Tyr Phe
                245                 250                 255

Leu

-continued

```
<210> SEQ ID NO 25
<211> LENGTH: 21
<212> TYPE: DNA
<213> ORGANISM: Artificial
<220> FEATURE:
<223> OTHER INFORMATION: synthetic

<400> SEQUENCE: 25
uuugucgccu gcaagagact t                                              21

<210> SEQ ID NO 26
<211> LENGTH: 21
<212> TYPE: DNA
<213> ORGANISM: Artificial
<220> FEATURE:
<223> OTHER INFORMATION: synthetic

<400> SEQUENCE: 26
gucucuugca ggcgacaaat t                                              21

<210> SEQ ID NO 27
<211> LENGTH: 21
<212> TYPE: DNA
<213> ORGANISM: Artificial
<220> FEATURE:
<223> OTHER INFORMATION: synthetic

<400> SEQUENCE: 27
uuacaggcuu cggccucuut t                                              21

<210> SEQ ID NO 28
<211> LENGTH: 21
<212> TYPE: DNA
<213> ORGANISM: Artificial
<220> FEATURE:
<223> OTHER INFORMATION: synthetic

<400> SEQUENCE: 28
aagaggccga agccuguaat t                                              21
```